(12) United States Patent
Haddad et al.

US009475914B2

(10) Patent No.: US 9,475,914 B2
(45) Date of Patent: Oct. 25, 2016

(54) POROUS POLYMER MONOLITHS, PROCESSES FOR PREPARATION AND USE THEREOF

(75) Inventors: Paul Raymond Haddad, Sandy Bay (AU); Emily Frances Hilder, Lenah Valley (AU); Esme Candish, Sandy Bay (AU); Mark A. J Bayliss, Kent (GB)

(73) Assignee: UNIVERSITY OF TASMANIA, Tasmania (AU)

( * ) Notice: Subject to any disclaimer, the term of this patent is extended or adjusted under 35 U.S.C. 154(b) by 0 days.

(21) Appl. No.: 13/520,546

(22) PCT Filed: Jan. 6, 2011

(86) PCT No.: PCT/AU2011/000008
§ 371 (c)(1),
(2), (4) Date: Jul. 16, 2012

(87) PCT Pub. No.: WO2011/082449
PCT Pub. Date: Jul. 14, 2011

(65) Prior Publication Data
US 2012/0276576 A1 Nov. 1, 2012

(30) Foreign Application Priority Data
Jan. 8, 2010 (AU) ................................ 2010900064

(51) Int. Cl.
| | |
|---|---|
| *C12Q 1/02* | (2006.01) |
| *C08J 9/14* | (2006.01) |
| *C08F 265/04* | (2006.01) |
| *C08L 33/06* | (2006.01) |
| *B01J 39/20* | (2006.01) |
| *B01J 41/14* | (2006.01) |
| *B01J 20/26* | (2006.01) |
| *B01J 20/285* | (2006.01) |
| *G01N 1/28* | (2006.01) |
| *B01J 20/28* | (2006.01) |

(52) U.S. Cl.
CPC ............... *C08J 9/142* (2013.01); *B01J 20/261* (2013.01); *B01J 20/264* (2013.01); *B01J 20/267* (2013.01); *B01J 20/285* (2013.01); *B01J 20/28042* (2013.01); *B01J 20/28057* (2013.01); *B01J 20/28083* (2013.01); *B01J 20/28085* (2013.01); *B01J 39/20* (2013.01); *B01J 41/14* (2013.01); *C08F 265/04* (2013.01); *C08L 33/066* (2013.01); *G01N 1/2813* (2013.01); *B01J 2220/82* (2013.01); *C08J 2207/10* (2013.01); *C08J 2333/06* (2013.01); *C08J 2333/14* (2013.01); *G01N 2001/2826* (2013.01)

(58) Field of Classification Search
None
See application file for complete search history.

(56) References Cited

U.S. PATENT DOCUMENTS

| | | | |
|---|---|---|---|
| 4,514,499 A | 4/1985 | Noll | |
| 4,965,289 A | 10/1990 | Sherrington et al. | |
| 5,130,343 A | 7/1992 | Frechet et al. | |
| 5,306,623 A | 4/1994 | Kiser | |
| 5,334,310 A | 8/1994 | Frechet et al. | |
| 5,336,599 A | 8/1994 | Kitajima | |
| 5,460,777 A | 10/1995 | Kitajima et al. | |
| 5,496,562 A | 3/1996 | Burgoyne | |
| 5,728,457 A | 3/1998 | Frechet et al. | |
| 5,756,126 A | 5/1998 | Burgoyne | |
| 5,929,214 A | 7/1999 | Peters et al. | |
| 5,939,259 A | 8/1999 | Harvey et al. | |
| 5,972,386 A | 10/1999 | Burgoyne | |
| 6,048,457 A | 4/2000 | Kopaciewicz et al. | |
| 6,303,290 B1 * | 10/2001 | Liu et al. ............. | 435/4 |
| 6,693,159 B1 * | 2/2004 | Holmes et al. ............. | 526/323.1 |
| 6,746,841 B1 | 6/2004 | Fomovskaia et al. | |
| 6,750,059 B1 | 6/2004 | Blakesley et al. | |
| 6,884,345 B1 * | 4/2005 | Irgum et al. ............... | 210/198.2 |
| 6,887,384 B1 | 5/2005 | Frechet et al. | |
| 7,024,890 B2 * | 4/2006 | Costa et al. ................ | 65/395 |
| 7,151,167 B2 | 12/2006 | Gjerde et al. | |
| 7,431,888 B2 | 10/2008 | Frechet et al. | |
| 7,479,223 B2 | 1/2009 | DiLeo et al. | |
| 7,731,844 B2 | 6/2010 | Mallet et al. | |
| 7,955,594 B2 * | 6/2011 | Greener ................... | 424/78.17 |
| 2003/0033930 A1 * | 2/2003 | Tom et al. ....................... | 95/45 |
| 2004/0060864 A1 | 4/2004 | Shepodd et al. | |
| 2004/0138323 A1 | 7/2004 | Stenzel-Rosebaum et al. | |
| 2005/0023456 A1 * | 2/2005 | Frechet et al. ............. | 250/288 |
| 2005/0032929 A1 * | 2/2005 | Greener .................... | 523/113 |
| 2005/0046086 A1 * | 3/2005 | Lee et al. ..................... | 264/444 |
| 2005/0116161 A1 * | 6/2005 | Hafeman et al. ............. | 250/282 |
| 2005/0226916 A1 | 10/2005 | Cochrum et al. | |
| 2006/0021939 A1 * | 2/2006 | Mallet et al. ................ | 210/656 |

(Continued)

FOREIGN PATENT DOCUMENTS

| | | |
|---|---|---|
| EP | 1245401 | 10/2002 |
| WO | WO-99-57599 | 11/1999 |

(Continued)

OTHER PUBLICATIONS

Rober et al., Analytica Chimica Acta, 644:95-103 (2009).*

(Continued)

*Primary Examiner* — Thomas J Visone
(74) *Attorney, Agent, or Firm* — Wilson Sonsini Goodrich & Rosati

(57) ABSTRACT

The present invention generally relates to porous polymer monoliths. The present invention also relates to processes for the preparation of porous polymer monoliths, storage mediums formed from porous polymer monoliths and use thereof in the drying and storage of body fluids including blood and blood plasma samples.

10 Claims, 7 Drawing Sheets

(56) References Cited

U.S. PATENT DOCUMENTS

| | | | |
|---|---|---|---|
| 2006/0042948 A1* | 3/2006 | Santiago et al. | 204/450 |
| 2006/0094015 A1* | 5/2006 | Smith et al. | 435/6 |
| 2006/0115384 A1 | 6/2006 | Wohleb | |
| 2006/0131238 A1* | 6/2006 | Xu | 210/656 |
| 2006/0247361 A1 | 11/2006 | Shah | |
| 2007/0092924 A1* | 4/2007 | Anderson | 435/23 |
| 2008/0035558 A1 | 2/2008 | Shah | |
| 2008/0081848 A1 | 4/2008 | Shih et al. | |
| 2008/0090295 A1* | 4/2008 | Feuerstein et al. | 436/54 |
| 2008/0160598 A1* | 7/2008 | Nozaki et al. | 435/283.1 |
| 2010/0009845 A1* | 1/2010 | Bonn et al. | 502/402 |
| 2010/0300972 A1* | 12/2010 | Mallet et al. | 210/656 |
| 2012/0107951 A1* | 5/2012 | Grenz et al. | 436/178 |
| 2013/0164856 A1* | 6/2013 | Jebrail et al. | 436/86 |

FOREIGN PATENT DOCUMENTS

| | | |
|---|---|---|
| WO | WO 00/14505 | 3/2000 |
| WO | WO-2005-017487 | 2/2005 |
| WO | WO 2005/102526 | 11/2005 |
| WO | WO-2006-092082 | 9/2006 |
| WO | WO-2006-118887 | 11/2006 |
| WO | WO-2011-082449 | 7/2011 |
| WO | WO-2011-137533 | 11/2011 |
| WO | WO-2013-006904 A1 | 1/2013 |

OTHER PUBLICATIONS

Gadre et al., Mater. Res. Soc. Symp. Proc. vol. 1237 (2010).*
Rober et al., Analytica Chimica Acta 644:95-103 (2009).*
Saunders et al., Analytica Chimica Acta 652:22-31 (2009).*
Uzen et al., Ind. Eng. Chem. Res., 43:6507-6513 (2004).*
Arrua et al., Mater., 2:2429-2466 (2009).*
Abdel-Rehim et al., "Evaluation of monolithic packed 96-tips and liquid chromatography-tandem mass spectrometry for extraction and quantification of pindolol and metoprolol in human plasma samples." Journal of Chromatography A, (2008), pp. 23-27: 1196-1197, Elsevier.
Allanson, et al., "Determination of rifampicin in human plasma and blood spots by high performance liquid chromatography with UV detection: a potential method for therapeutic drug monitoring," Journal of Pharmaceutical and Biomedical Analysis, 2007, 44(4): pp. 963-969.
Bakry et al., "Monolithic porous polymer layer for the separation of peptides and proteins using thin-layer chromatography coupled with MALDI-TOF-MS" Analytical Chemistry, 2007, 79(2): pp. 486-493.
Bisjak et al., "Amino-functionalized monolithic poly(glycidyl methacrylates-co-divinylbenzene) Ion-exchange stationary phases for the separation of oligonucleotides," Chromatographia, 2005, 62 (Supplement 13); S31-36.
Brunauer, et al., "Adsorption of Gases in Multimolecular Layers," Journal of the American Chemical Society, 1938. vol. 60: p. 309-319.
Corso, et al., "Neutral loss analysis of Amino Acids by desorption electrospray ionization using an unmodified tandem quadruple mass spectrometer," Rapid Communications in Mass Spectrometry, 2007. 21: p. 3777-3784.
Davankov et al., "Polymeric adsorbent for removing toxic proteins from blood of patients with kidney failure." Journal of Chromatography B, (2000), pp. 73-80: 739, Elsevier.
Edelbroek, et al., "Dried Blood Spot Methods in Therapeutic Drug Monitoring: Methods, Assays, and Pitfalls," Therapeutic Drug Monitoring, 2009, 31(3): p. 327-336.
Eeltink, et al., Controlling the surface chemistry and chromatographic properties of methacrylate-ester-based monolithic capillary columns via photografting, J. Sep. Sci., 2007, 30(3), 407-413.

Hambidge, Michael, "Biomarkers of Nutritional Exposure and Nutritional Status: Biomarkers of Trace Mineral Intake and Status," Journal of Nutrition, 2003. 133(3): p. 9485-9555.
Nordberg, et al., "Recent advances in polymer monoliths for ion-exchange chromatography," Analytical and Bioanalytical Chemistry, 2009, 394(1): pp. 71-84.
PCT/AU2012/000826 International Search Report dated Aug. 13, 2012.
PCT/AU2011/000008 International Preliminary Report on Patentability dated Nov. 15, 2011.
PCT/AU2011/000008 International Search Report dated Feb. 4, 2011.
Potter, et al., "Porous Polymer monoliths for extraction: Diverse applications and platforms," J. Sep. Sci., 2008, vol. 31, pp. 1881-1906.
Qu et al., "Preparation and Characterization of Large Porous Poly (HEMA-co-EDMA) Microspheres with Narrow Size Distribution by Modified Membrane Emulsification Method." Journal of Applied Polymer Science (2007) pp. 1632-1641: 105.
Rober et al., "New 3-D microarray platform based on macroporous polymer monoliths." Analytica Chimica Acta 644 (2009): 95-103, Elsevier.
Saunders, et al., "Separation and sample pre-treatment in bioanalysis using monolithic phases: A review." Analytica Chimica Acta 652 (2009): 22-31 Elsevier.
Svec, et al., "Kinetic Control of Pore Formation in Macroporous polymers. Formation of "Molded" Porous Materials with High Flow Characteristics for Separations or Catalysis," 1995, 7(4): pp. 707-715.
Thabano et al., "Selective extraction and elution of weak bases by in-line solid-phase extraction capillary electrophoreses using a pH step gradient and a weak cation-exchange monolith," The Analyst, 2008, 133(10), 1380-1387.
Ueki et al., "Preparation and application of methacrylate-based cation-exchange monolithic columns for capillary ion chromatography," Analytical Chemistry, 2004, 76(23): pp. 7007-7012.
Xie, et al., "Porous Polymer Monoliths: Preparation of Sorbent Materials with High-Surface Areas and Controlled Surface Chemistry for High-Throughput, Online, Solid-Phase, Extraction of Polar Organic Compounds," 2008, Chem. Mater., vol. 10, No. 12, pp. 4072-4078.
Yu, et al, "Preparation of Monolithic Polymers with Controlled Porous Properties for Microfluidic Chip Applications Using Photoinitiated Free-Radical Polymerization," Journal of Polymer Science: Part A: Polymer Chemistry, 2002, vol. 40, pp. 755-769.
EP11731623 Supplementary EP Search Report dated Jun. 5, 2013.
PCT/AU2012/000826 International Preliminary Report on Patentability dated Jan. 23, 2014.
Uyama, Y. et al., "Surface Modification of Polymers by Grafting" Adv. Polym. Sci. 1998, vol. 137, pp. 1-39.
Viklund, C. et al. "Synthesis of Porous Zwitterionic Sulfobetaine Monoliths and Characterization of Their Interaction with Proteins" Macromolecules 2000, vol. 33, No. 7, pp. 2539-2544.
EP12811104.4 Supplementary EP Search Report dated Jan. 28, 2015.
Altun et al. Monolithic methacrylate packed 96-tips for high throughput bioanalysis. Journal of Chromatography, 1217:2581-2588 (2010).
Holdsvendova et al. Hydroxymethyl methacrylate-based monolithic columns designed for separation of oligonucleotides in hydrophilic-interaction capillary liquid chromatography. J Biochem Biophys Methods 70:23-29 (2007).
U.S. Appl. No. 14/151,689 Office Action dated Jun. 1, 2015.
U.S. Appl. No. 14/151,689 Office Action dated Dec. 8, 2015.

* cited by examiner

POROUS POLYMER MONOLITHS, PROCESSES FOR PREPARATION AND USE THEREOF

CROSS REFERENCE TO RELATED APPLICATION

This application is a U.S. national stage entry under 35 USC 371(c) of PCT/AU2011/000008, filed Jan. 6, 2011, which claims the benefit of Australian Patent Application No. 2010900064, filed Jan. 8, 2010, the contents of which are herein incorporated by reference in their entirety.

FIELD

The present invention generally relates to porous polymer monoliths. The present invention also relates to processes for the preparation of porous polymer monoliths, storage mediums formed from porous polymer monoliths and use thereof in the drying and storage of body fluids including blood and blood plasma samples.

BACKGROUND

The sampling technique known as dried blood spotting (DBS) was developed by the microbiologist Robert Guthrie in 1963. The sample collection procedure is simplistic, involving the collection of a very small volume of blood from a small incision to the heel or finger. A drop of blood is then directly applied to a sampling paper and dried for future analyte extraction. DBS sampling is now a common and established practice for the quantitative and qualitative screening of metabolic disorders in newborns (Edelbroek, P. M., J. van der Heijden, and L. M. L. Stolk, *Dried Blood Spot Methods in Therapeutic Drug Monitoring: Methods, Assays, and Pitfalls*. Therapeutic Drug Monitoring, 2009. 31(3): p. 327-336).

Conventional sampling techniques employ plasma or serum as the biological matrix of choice for analysis. These techniques require large volumes of blood to be collected directly from the vein of a test subject. Conversely, DBS sampling requires substantially smaller sample volumes (microliters as opposed to milliliters) which allows sample collection in situations where collection in the traditional manner may be difficult and is now routinely applied to epidemiological studies, and for example has been successfully implemented for assaying numerous biological markers such as amino acids (Corso, G., et al., *Rapid Communications in Mass Spectrometry*, 2007. 21(23): p. 3777-3784), and trace elements (Hambidge, M., Journal of Nutrition, 2003. 133(3): p 9485-9555).

DBS methodologies are particularly suitable for the analysis of infectious agents such as HIV and HCV, as the reduced sample volumes minimize the risk of infection and blood is no longer considered to be a biohazard once dried, which drastically simplifies the storage and transportation of samples (Allanson, A. L., et al., Journal of Pharmaceutical and Biomedical Analysis, 2007, 44(4): p 963-969). Without specialised storage requirements samples can be easily and cost effectively transported around the world. The technique affords a further advantage in that equipment such as centrifuges and freezers are not required for sample processing or storage.

DBS technologies have also been applied in pharmacokinetic analysis, for example, used in solid phase extraction (SPE) to analyse components in blood.

The medium currently used in DBS methodologies, which involves the drying and storage of blood and plasma samples prior to future extraction and analysis, comprises paper based cellulose materials. For example, modified paper based materials have been developed for simplified isolation of nucleic acid; where the paper is chemically treated with a range of compounds to promote the long term storage of DNA. However, paper based cellulose materials are not particularly suited to accelerated drying procedures, particularly with blood plasma, and are not suited to incorporating specific functionalities to facilitate extraction of selective components from blood.

There is consequently a need to identify alternative materials that provide properties for facilitating the drying and storage of biological fluids, such as blood and plasma samples, for future extraction and analysis, or to allow specific functionality to be incorporated into the storage medium.

SUMMARY

In a first aspect, there is provided a use of a porous polymer monolith as a medium for drying and storage of a body fluid.

In a second aspect, there is provided a method of storing a body fluid for future analysis comprising applying a body fluid sample to a porous polymer monolith medium and drying the body fluid such that the sample at least partially solidifies and adsorbs or adheres to the porous polymer monolith medium.

In a third aspect, there is provided a method of storing a body fluid for future analysis comprising:
 applying one or more body fluid samples to one or more regions of a porous polymer monolith medium;
 partially drying the one or more samples applied to the medium;
 separating any one or more regions of the porous polymer monolith having sample applied thereto from regions without sample applied thereto;
 further drying the one or more samples applied to the one or more regions of the medium; and
 storing the one or more samples applied to the one or more regions of the medium.

In an embodiment, the separating of any one or more regions of the porous polymer monolith having sample applied thereto from regions without sample applied thereto, may comprise substantially removing any medium not having body fluid applied thereto from around the sample, for example trimming or cutting away medium at or near the perimeter of the sample. The medium may be trimmed or cut away from around the sample such that the sample substantially covers the surface of the region to which the sample was applied.

The method may further comprise the identification and detection of an analyte from the stored sample applied to the medium. In an embodiment, the stored body fluid sample can be analysed without pre-treatment and/or removal from the porous polymer monolith medium. In another embodiment, the method can comprise pre-treating the sample stored on the porous polymer monolith before analysing the sample thereof.

In an embodiment, the drying of the body fluid, such as blood or blood plasma, is enhanced by application of at least one of elevated temperature, forced convection or reduced pressure. The elevated temperature may be in a temperature range above ambient but below the temperature at which the integrity of storage medium or sample is compromised. In a particular embodiment the elevated temperature is in the range between 30 and 150° C., 40 and 120° C., and more particularly between about 60 and 100° C., or at 30° C. and above, 50° C. and above, 70° C. and above, 90° C. and above, 110° C. and above, or 130° C. and above. In a particular embodiment the elevated temperature is above about 90° C. In another particular embodiment, the reduced pressure is in the range of 5 to 760 mmHg.

In a fourth aspect, there is provided a method of analysis involving the identification and detection of an analyte from a stored body fluid sample adsorbed or adhered to a porous polymer monolith medium.

In an embodiment, the stored body fluid sample is analysed without pre-treatment and/or removal from the porous polymer monolith medium. The analysis is typically for analytes. The analytes can include small molecules and low molecular weight compounds present in blood or blood plasma samples, for example, pharmaceutical agents including new chemical entities (NCEs) and any metabolites thereof, peptides, proteins, oligonucleotides, oligosaccharides, lipids or other labile compounds. In another embodiment, the analysis involves the simultaneous analysis of at least two analytes. In a particular embodiment, the at least two analytes comprise an NCE and a metabolite thereof.

In a fifth aspect, there is provided a body fluid storage medium comprising a porous polymer monolith having an integral body with a pore size and/or specific surface area adapted to facilitate the drying and storage of body fluids.

The porous polymer monolith or medium thereof according to the above embodiments is capable of receiving a body fluid in liquid form and subsequently being dried to facilitate storage, transport and/or future analysis of the body fluid. In a particular embodiment, the porous polymer monolith or medium thereof is adapted for storing blood and/or blood plasma.

In an embodiment, the pore size of the porous polymer monolith is in the range of 5 to 10,000 nm, 50 to 5,000 nm, 100 to 2,000 nm, 200 to 1000 nm. A smaller pore size correlates to a higher surface area that facilitates the adsorption of body fluids such as blood and blood plasma. In another embodiment, the specific surface area of the porous polymer matrix when measured by nitrogen adsorption using BET isotherm is in the range of 0.5 to 1000 $m^2/g$, 1 to 500 $m^2/g$, 5 to 200 $m^2/g$, 10 to 100 $m^2/g$, 20 to 60 $m^2/g$, 30-50 $m^2/g$.

In another embodiment, the porous polymer monolith comprises a copolymer of a polyvinyl monomer and a monovinyl monomer. The porous polymer monolith can be formed from one or more acrylic acid monomers, which may be optionally functionalised, for example, with a group selected from sulphonyl, phosphonyl, carboxyl, amino and nitro. In a particular embodiment, the acrylic acid monomers are optionally functionalised methacrylates. The optionally functionalised methacrylates can be selected from at least one of hydroxyethylmethacrylate, methacrylic acid, ethylene glycol dimethacrylic acid, or combinations thereof.

In another embodiment, functionality can be incorporated into the porous polymer monolith for in situ elimination of undesirable components in blood that impede the detection of other particular components, for example analytes such as pharmaceutical agents or new chemical entities (NCE). In one particular embodiment, at least the surface of the porous polymer monolith is modified to provide ion exchange properties to facilitate post-storage analysis of any analytes present in the sample. In another particular embodiment, the surface area of the porous polymer monolith can be provided with ion exchange properties to facilitate the adherence thereon of selected pharmaceutical agents or non-adherence of selected contaminants present in the body fluid. The porous polymer monolith may therefore be used to analyse body fluids dried thereon without the need for chemical based pre-treatment. In another particular embodiment, the ion exchange properties may be provided by functional groups present on a monomer from which the porous polymer matrix is formed, and/or a post polymerisation surface modification comprising co-polymerisation grafting or other chemical modification.

In another embodiment, the body fluid storage medium is obtained from a polymerization mixture comprising about 10-40 vol % of a monovinyl monomer, 10 to 40 vol % of a polyvinyl monomer, about 20-80 vol % porogens and about 1 vol % initiator.

The body fluid storage medium can also comprise the porous polymer monolith and at least a flexible polymer layer, for example a flexible polymer backing layer.

In a sixth aspect, there is provided a process for preparing a body fluid storage medium by polymerizing a polymerization mixture comprising at least a polyvinyl monomer in the presence of an initiator and a porogen. In one embodiment, the polymerization mixture further comprises a monovinyl monomer.

In a seventh aspect, there is provided a method for storing and subsequent analysis of a body fluid sample comprising genetic material, the method comprising:

applying a body fluid sample comprising one or more analytes to a porous polymer monolith, the porous polymer monolith defined according to any one of the above described embodiments;

drying the sample applied to the porous polymer monolith;

storing the sample;

retrieving the sample;

optionally pre-treating the sample; and analysing the sample for the one or more analytes.

In a further embodiment of any one of the above embodiments or aspects, the porous polymer monoliths are used for the storage of whole blood, or for dried blood spotting (DBS).

In a further embodiment of any one of the above embodiments or aspects, the porous polymer monoliths are used for the storage of blood plasma, or for dried blood plasma spotting (DPS).

BRIEF DESCRIPTION OF THE DRAWINGS

Preferred embodiments of the present invention will now be further described and illustrated, by way of example only, with reference to the accompanying drawings in which.

DETAILED DESCRIPTION OF THE ABBREVIATIONS

Figure 1A:
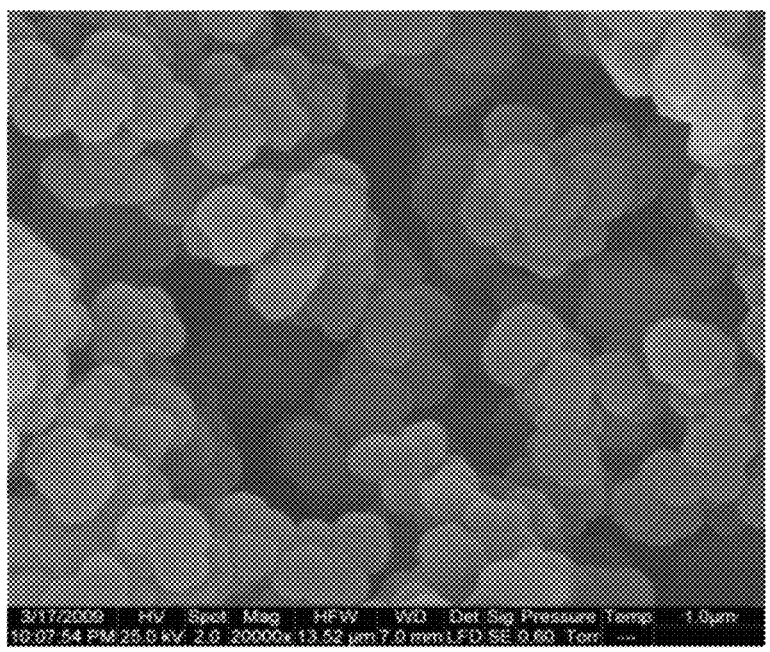
FIGS. 1a and 1b show SEM images of the poly(HEMA-co-EDMA) monolith utilised as a sorbent for DBS and DPS, 20 000× magnification (FIG. 1a) of the bulk monolith and 3000× magnification (FIG. 1b) of the glass cover slide.

In the Examples, reference will be made to the following abbreviations in which:
AFM Atomic Force Microscopy
APP Applications
C Celsius
Cl Class
[ ] Concentration
EMAA polyethylene methacrylic acid
F Fahrenheit
FTIR Fourier Transform Infrared
h Hour
Mn Number average molecular weight
Mw Weight average molecular weight
MW Molecular weight
RH Relative Humidity
SEM Scanning Electron Microscopy
SENB single edge notched_bar
TDCB tapered double cantilever beam
TETA triethyltetramine
Wt % weight percentage of specific component in composition
XPS X-Ray Photoelectron Spectroscopy
DEGDMA diethylene glycol dimethacrylate
DMPAP 2,2-dimethoxy-2-phenyl-acetophenone
EDMA ethylene glycol dimethacrylate
GMA glycidyl methacrylate
HEMA 2-hydroxyl ethyl methacrylate
MAA methacrylic acid
γ-MAPS 3-(trimethoxysilyl) propyl methacrylate
META methacryloyloxyethyl trimethylammonium chloride
SPMA 3-sulfopropyl methacrylate
UK258300 Reference compound
UK280111 Reference compound

DETAILED DESCRIPTION

In an attempt to identify alternative materials that provide properties for facilitating the drying and storage of biological fluids for future extraction and analysis, such as blood and plasma samples, and to identify materials that may allow specific functionality to be incorporated therein, it has now been found that a body fluid storage medium can be formed from a porous polymer monolith. The non-limiting particular embodiments of the present invention are described as follows.

The present invention generally relates to the use of a porous polymer monolith as a medium for storing a dried body fluid, particularly blood and blood plasma. The porous polymer monoliths described herein can therefore provide an appropriate medium for use in DBS methodologies, as an alternative to the paper based cellulose materials currently being used. In particular embodiments the porous polymer monoliths provide an improved medium for use in storing biological matter for later analytical examination, such as storage of blood and plasma samples for future detection and identification of analytes including small molecules, such as pharmaceutical agents and associated metabolites, and low molecular weight compounds such as proteins and oligonucleotides. The porous polymer monoliths have excellent properties that have been identified to enable the efficient drying and long term storage of body fluid samples including blood and blood plasma.

A further advantage of employing the porous polymer monoliths as a sorbent for DBS is that these materials allow a degree of control over the morphology and surface chemistry of the materials.

TERMS

A "porous polymer monolith" generally refers to a continuous porous polymer matrix having an integral body with a particular pore size range. The polymer matrix is adapted to facilitate the adsorption or adherence of body fluids, particularly blood and blood plasma.

A "body fluid" refers to any fluid that can be taken as a sample from the body of an organism and which may contain a detectable analyte, for example blood or blood plasma from a human or animal subject.

An "analyte" includes but is not limited to small molecules and low molecular weight compounds that may be detected in a body fluid, such as a pharmaceutical agent present in a blood or blood plasma sample obtained from a human or animal subject. For example, an "analyte" may include pharmaceutical agents including NCEs, peptides, proteins, oligonucleotides, oligosaccharides, lipids or other labile compounds.

The term "porous polymer monolith medium", "body fluid storage medium", "storage medium" or like term generally refers to a medium comprising the porous polymer monolith, which includes the porous polymer monolith by itself or further associated with a support material or matrix.

A "support material", "support matrix" or like term, is a supporting layer or structure that may be associated with the polymer monolith by attachment, removable attachment, or non-attachment, for example, the polymer monolith may be polymerised on the support material or may merely sit upon the support material with or without other intervening layers that may also be associated with the polymer monolith and support material by way of attachment, removable attachment, or non-attachment. The support material or matrix may be flexible, semi-rigid or rigid and may be in any desired form, such as a film or membrane, and may be formed from any appropriate material including glass, polymers, metals, ceramics, or combination thereof.

The term "alkyl" means any saturated or unsaturated, branched or unbranched, cyclised, or combination thereof, typically having 1-10 carbon atoms, which includes methyl, ethyl, propyl, isopropyl, butyl, isobutyl, t-butyl, pentyl, cyclopentyl, isopentyl, neopentyl, hexyl, isohexyl, cyclohexyl, which may be optionally substituted with methyl.

The term "alkylene" means any branched or unbranched, cyclised, or combination thereof, typically having 1-10 carbon atoms, which includes methyl, ethyl, propyl, isopropyl, butyl, isobutyl, t-butyl, pentyl, cyclopentyl, isopentyl, neopentyl, hexyl, isohexyl, cyclohexyl, which may be optionally substituted with methyl.

The term "polymer" includes copolymers, and the term "monomer" includes co-monomers.

The term "porogen", "porogenic solvent" or like term, refers to a solvent capable of forming pores in a polymer matrix during polymerization thereof, and includes but is not limited to aliphatic hydrocarbons, aromatic hydrocarbons, esters, amides, alcohols, ketones, ethers, solutions of soluble polymers, and mixtures thereof.

The term "initiator" refers to any free radical generator capable of initiating polymerization by way of thermal initiation, photoinitiation, or redox initiation.

Porous Polymer Monoliths

Porous polymer monoliths are typically highly crosslinked structures that can function as a stationary support. The internal structure of polymer monoliths consists of a fused array of microglobules that are separated by pores and their structural rigidity is secured by extensive crosslinking. Polymer monoliths can be fabricated from a mixture containing an initiator and monomers (including crosslinking monomers) dissolved in the pore-forming solvents known as porogens. Formation of the monolith is triggered by a breakdown of the initiator by an external source (e.g. photoinitiation) creating a radical which induces the formation of polymer chains that precipitate out of the polymerization mixture eventually agglomerating together to form a continuous solid structure. The morphology of the monolith can be controlled by numerous variables; the crosslinking monomer(s) employed, the composition and percentage of the porogenic solvents (porogens), the concentration of the free-radical initiator and the method used to initiate polymerization.

As polymer monoliths are typically continuous rigid structures, they can be readily fabricated in situ in a range of formats, shapes or sizes. Monoliths have been typically fabricated within the confines of chromatographic columns or capillaries for numerous chromatographic applications. However, given an appropriate mould it is also possible to fabricate monoliths in the format of flat sheets. Flat monolithic sheets provide a particularly suitable medium for the storage of whole blood which allows for ease in both storage and transportation of blood samples.

A further advantage of using polymeric monoliths for DBS stems from the ability to be able to control both the porous properties and the specific surface chemistries. The ability to incorporate specific functionality to the monolith surface allows for the specific extraction of analytes, for example pharmaceutical agents or new chemical entities (NCE), as well as facilitating matrix elimination that may degrade future analysis. Future analysis may include solid phase extraction (SPE), which is based on physisorption of analytes on a suitable medium and thus to obtain maximum analyte recovery the medium should possess a large surface area. The porous properties of the medium can also be used to control the specific surface chemistry to a degree as the surface area and thus the ion-exchange capacity of the medium is dependent on the porous properties. The detection and identification of analytes may include small molecules and low molecular weight compounds present in the blood or blood plasma samples, for example, pharmaceutical agents including NCEs, peptides, proteins, oligonucleotides, oligosaccharides, lipids or other labile compounds.

In one embodiment, the porous polymer monolith is a macroporous structure having a percent porosity of about 45 to 85%, more particularly between about 60 and 75%.

In an embodiment, the pore size of the porous polymer monolith can be in the range of 5 to 10,000 nm, 50 to 5,000 nm, 100 to 2,000 nm, 200 to 1000 nm. A smaller pore size correlates to a higher surface area that facilitates the adsorption of body fluids such as blood and blood plasma. In another embodiment, the specific surface area of the porous polymer matrix when measured by nitrogen adsorption using BET isotherm (Atkins P, *Physical Chemistry*, Oxford University Press) is in the range of 0.5 to 1000 $m^2/g$, 1 to 500 $m^2/g$, 5 to 200 $m^2/g$, 10 to 100 $m^2/g$, 20 to 60 $m^2/g$, 30-50 $m^2/g$.

In one embodiment, the porous polymer monolith can be formed from one or more acrylic acid monomers. The acrylic acid monomers may be optionally substituted with a $C_{2-20}$ carbon chain having one or more functional groups selected from sulphonyl, phosphonyl, carboxyl, amino and nitro. In a particular embodiment, the acrylic acid monomers are methacrylates, and more particularly are selected from at least one of hydroxyethylmethacrylate, methacrylic acid, ethylene glycol dimethacrylic acid, or mixtures thereof.

In another embodiment, the porous polymer monolith can comprise a crosslinked polyvinyl monomer or a copolymer of a polyvinyl monomer and a monovinyl monomer.

In one embodiment, the porous polymer monolith can be prepared by polymerizing a polymerization mixture comprising at least a polyvinyl monomer in the presence of an initiator, and a porogen. In a particular embodiment, the polymerization mixture further comprises a monovinyl monomer. The polymerization mixture may be disposed on the matrix support and polymerization can be initiated thereon so as to form a porous polymer monolith, which can then be washed with a suitable solvent to remove the porogen. The polymerization mixture can also be prepared and polymerized first and then disposed upon the matrix support.

The polymerization mixture can be comprised of a polyvinyl monomer in an amount of about 10 to 60 vol %, and more particularly from about 15 to 40 vol %, about 45-85 vol % porogens and about 1 vol % initiator. In one embodiment, the polymerization mixture is comprised of about 10-40% of a monovinyl monomer, 10 to 40 vol % of a polyvinyl monomer, about 20-80 vol % porogens and about 1 vol % initiator. The ranges of each of the monomers, crosslinkers and porogens can be varied depending on the intended use.

The polyvinyl monomers can include one or more monomers selected from the group consisting of alkylene diacrylates, alkylene diacrylamides, alkylene dimethacrylates, alkylene diacrylamides, alkylene dimethacrylamides, hydroxyalkylene diacrylates, hydroxyalkylene dimethacrylates, wherein the alkylene group in each of the aforementioned alkylene monomers consists of 1-10 carbon atoms, oligoethylene glycol diacrylates, oligoethylene glycol dimethacrylates, vinyl esters of polycarboxylic acids, divinylbenzenes, divinylnaphthalenes, pentaerythritol dimethacrylates, pentaerythritol trimethacrylates, or pentaerythritol tetramethacrylates, pentaerythritol diacrylates, pentaerythritol triacrylates, pentaerythritol tetraacrylates, trimethylopropane trimethacrylates and trimethylopropane acrylates. In a particular embodiment the polyvinyl monomer can be selected from ethylene dimethacrylate and/or divinylbenzene. In another particular embodiment, the polyvinyl monomer is methylene glycol dimethacrylic acid.

In one embodiment, the monovinyl monomers include but are not limited to styrene, vinylnaphthalene, vinylanthracene and their ring substituted derivatives wherein the substituents include chloromethyl, alkyls with up to 18 carbon atoms, hydroxyl, t-butyloxycarbonyl, halogen, nitro, protected hydroxyls or amino groups. Other monomers useful to form the monolithic matrix include but are not limited to, acrylamides, and methacrylamides and their derivatives substituted on the nitrogen atom with one or two $C_{1-5}$ alkyls, $C_{1-4}$ alkylaminoalkyls or dialkylaminoalkyls, $C_{1-4}$ methoxyaminoalkyls, $C_{1-4}$ dimethoxy or diethoxyaminoalkyls, $C_{1-4}$ methoxyalkyls, tetrahydropyranyl, and tetrahydrofurfuryl groups, N-acryloylpiperidine and N-acryloylpyrrolidone, and mixtures thereof.

In another embodiment, the monovinyl monomer may also be selected from the group consisting of acrylic and methacrylic acid esters, alkyl acrylates, alkyl methacrylates, perfluorinated alkyl acrylates, perfluorinated alkyl methacrylates, hydroxyalkyl acrylates, hydroxyalkyl methacrylates, wherein the alkyl group in each of the aforementioned alkyls consists of 1-10 carbon atoms, sulfoalkyl acrylates, sulfoalkyl methacrylates, oligoethyleneoxide acrylates, oligoethyleneoxide methacrylates, and acrylate and methacrylate derivatives including primary, secondary, tertiary, and quarternary amine, epoxide and zwitterionic functionalities, and vinylacetate, vinylpyrrolidone, vinylazlactone.

In a particular embodiment, the monovinyl monomer can be selected from the group consisting of butyl methacrylate, benzyl methacrylate and styrene. In another particular embodiment, the monovinyl monomer can be selected from hydroxyethylmethacrylate and/or methacrylic acid.

Examples of suitable polymers used for forming the porous polymer monoliths include poly(HEMA-co-EDMA), poly(EDMA-co-MAA), poly(HEMA-co-EDMA-co-SPMA), poly(GMA-co-DEGDMA).

Flat monolith sheets can be successfully fabricated, for example, by anchoring the thin sheet of monolith to a rigid glass plate by imparting methacryloyl functionalities to the surface of the glass. The methacyloyl functionalities participate in the polymerization process resulting in the covalent attachment of the monolith to the glass slide during the polymerization process. The porous polymer monoliths may also be associated with other support materials, for example adherence with flexible, semi-rigid or rigid polymeric films.

In one embodiment, the porous polymer monoliths are associated with a support material or layer. This association may be by attachment, removable attachment, or non-attachment. In another embodiment, the support material or layer is flexible. The support material may be a backing layer. In another embodiment, the support material or layer comprises a polymer material, for example a thermoplastic material such as a flexible polymer layer, which may comprise a polyolefin, for example a polyolefin selected or formed from polyethylene, polypropylene or a cyclic olefin copolymer based material. Polyolefin polymers can provide improved chemical inertness over other materials such as glass.

In one embodiment, the porous polymer monolith or medium thereof is a sheet or film of up to about 1 mm in thickness, particularly between about 300 and 600 µm in thickness, and more particularly about 500 µm in thickness. Other forms and thickness of monolith or monolith medium are contemplated and may be formed depending on the specific use, for example the type of post storage anaylsis contemplated.

Preferred polymer monoliths are based on acrylate/methacrylate and styrene monomers, which provide properties suitable for the extraction of analytes from complicated matrices. A preferred polymer monolith contains methacrylate moieties because this affords a greater degree of flexibility. In addition, the aliphatic methacryloyl monomers are UV transparent and therefore photo-initiated polymerization can be implemented to fabricate the sorbents.

Other preferred polymers include polymers with functional groups incorporated along the backbone of the polymer to facilitate further modification or interaction with blood or blood plasma. For example, a porous polymer monolith sheet can be configured to enable multiple blood spot samples to be provided thereon, and optionally configured to facilitate removal of excess monolith from around each blood spot sample.

Photo-initiated polymerization is an attractive approach for monolith synthesis as it is very rapid; a material may be fabricated in less than an hour. In larger scale commercial manufacture the polymerization and fabrication processes are typically continuous and can have shorter residence times such as in the order of seconds or minutes. Additionally, the approach affords spatial control, enabling the formation of the polymeric monolith within a specifically defined space. The mechanism involves the photoexcitation of the initiator to create a radical which begins the formation of polymer chains. The polymer chains precipitate out of the solution and eventually agglomerate together forming a highly crosslinked polymeric monolithic structure. Essentially the porogens (porogenic solvents) are a mixture that is a non-solvent for the polymer, where the polymer precipitates out, leaving pores behind in the polymer matrix of the monolith.

The porous properties of a polymer monolith prepared by photo-initiation can be controlled by a number of variables including the exposure time and the lamp intensity. As well, other controllable variables include the percentage of cross-linker, the concentration of initiator and composition and percentage of the porogenic solvents. Altering the porogens affects only the porous structure of the material while varying the other parameters modifies the composition and the rigidity of the material. Increasing the concentration of the non-solvent porogen induces precipitation early in the polymerization procedure which typically results in material with a larger pore size. Thus the choice of porogenic solvents and their relative compositions are chosen to engineer a material of the desired porous structure.

The composition and percentage of porogenic solvent can be used to control the porous properties by changing or adjusting the percentage of the porogenic solvent mixture with a co-porogen, such as cyclohexanol, propanol, water, or butanediol. This affects both median pore size and pore volume of the resulting monoliths. A broad range of pore sizes can easily be achieved by simple adjustments in the composition of porogenic solvent.

In one embodiment, the porogen used to prepare the porous polymer monolith may be selected from a variety of different types of materials. For example, suitable liquid porogens include aliphatic hydrocarbons, aromatic hydrocarbons, esters, amides, alcohols, ketones, ethers, solutions of soluble polymers, and mixtures thereof. The porogen is generally present in the polymerization mixture in an amount of from about 40 to 90 vol %, more preferably from about 50 to 80 vol %. In a particular embodiment, the porogen or porogenic solvents include dodecanol, cyclohexanol, methanol, hexane, or mixtures thereof. In a preferred embodiment, the porogen is 1-decanol or cyclohexanol. In another particular embodiment, the porogenic solvent comprises at least 35% dodecanol in combination with cyclohexanol.

The percent porosity is the percentage of pore volume in the total volume of the monolithic matrix. The term "pore volume" as used herein refers to the volume of pores in 1 g of the monolith. In one embodiment, the porous polymer monolith is a macroporous structure having a percent porosity of about 45 to 85%, more particularly between about 60 and 75%. In another embodiment, the pore size of the porous polymer monolith can be in the range of 5 to 10,000 nm, 50 to 5,000 nm, 100 to 2,000 nm, 200 to 1000 nm. A smaller pore size correlates to a higher surface area that facilitates the adsorption of body fluids such as blood and blood plasma. In another embodiment, the specific surface area of the porous polymer matrix when measured by nitrogen adsorption using BET isotherm (Atkins P, *Physical Chemistry*, Oxford University Press) is in the range of 0.5 to 1000 $m^2/g$, 1 to 500 $m^2/g$, 5 to 200 $m^2/g$, 10 to 100 $m^2/g$, 20 to 60 $m^2/g$, 30-50 $m^2/g$.

Polymerization can be carried out through various methods of free radical initiation mechanisms including but not limited to thermal initiation, photoinitiation, redox initiation. In one embodiment, about 0.1-5 wt % (with respect to the monomers) of free radical or hydrogen abstracting photoinitiator can be used to create the porous polymer monolithic matrix. For example, 1 wt % (with respect to monomers) of a hydrogen abstracting initiator can be used to initiate the polymerization process. Hydrogen abstracting photoinitators may include benzophenone, 2,2-dimethoxy-2-phenylacetophenone (DMPAP), dimethoxyacetophenone, xanthone, and thioxanthone. If solubility of the chosen photoinitiator is poor, desired concentration of the initiator can be achieved by adding a surfactant that enables the homogenization of the initiator in emulsions with higher initiator concentration.

In another embodiment, whereby polymerization is carried out by thermal initiation, the thermal initiator is generally a peroxide, a hydroperoxide, peroxo- or an azocompound selected from the group consisting of benzoylperoxide, potassium peroxodisulfate, ammonium peroxodisulfate, t-butyl hydroperoxide, 2,2'-azobisisobutyronitrile (AIBN), and azobisiocyanobutyric acid and the thermally induced polymerization is performed by heating the polymerization mixture to temperatures between 30° C. and 120° C.

In another embodiment, whereby polymerization is initiated by a redox initiator, the redox initiator may be selected from the group consisting of mixtures of benzoyl peroxide-dimethylaniline, and ammonium peroxodisulfate-N, N, N', N'-tetramethylene-1, 2-ethylenediamine.

The incorporation of HEMA into the polymer monolith increases the polarity of the surface and thus the wettability. As blood is composed predominantly of water, the incorporation of the polar monomer into the monolith is beneficial for the adsorption of the blood.

Varying the type and amounts of porogenic solvents can provide control over the pore size distribution of the monoliths, which can be examined by mercury intrusion porosimetry (MIP). HEMA is a polar monomer and increasing the concentration of a less polar porogen, such as 1-dodecanol, typically provides monoliths with larger pores.

It was found that increasing the percentage of dodecanol between 38-100% of porogenic solvent in a mixture of dodecanol and cyclotextarol maintained the pore size distribution at approximately 600 nm. A binary porogenic solvent of methanol and hexane at equal ratios was employed to achieve large pores in the poly(HEMA-co-EDMA) monolith. The pore size distribution achieved was 7087 nm. Monoliths with a smaller pore size were more reproducible, for example poly(HEMA-co-EDMA) monolith containing a binary porogenic solvent of 40% dodecanol and 20% cyclohexanol, and were developed as a potential sorbent for the storage of whole blood and plasma.

The visual appearance of the monolith is considered to be a reliable indicator of the pore size due to light scattering. The monoliths studied appeared chalky which indicated a macroporous material (i.e. above about 50 nm pore size). Analysis by MIP confirmed this, with the median pore diameter measured at about 600 nm and the monolith porosity being 68%. The specific surface area for the monolith was determined by BET analysis.

Figure 1B:
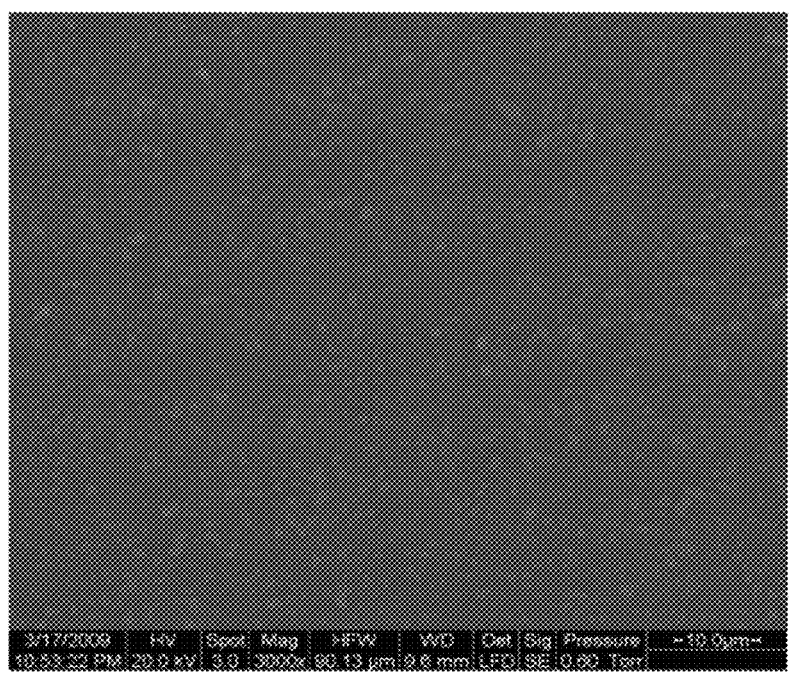
Figure 2:
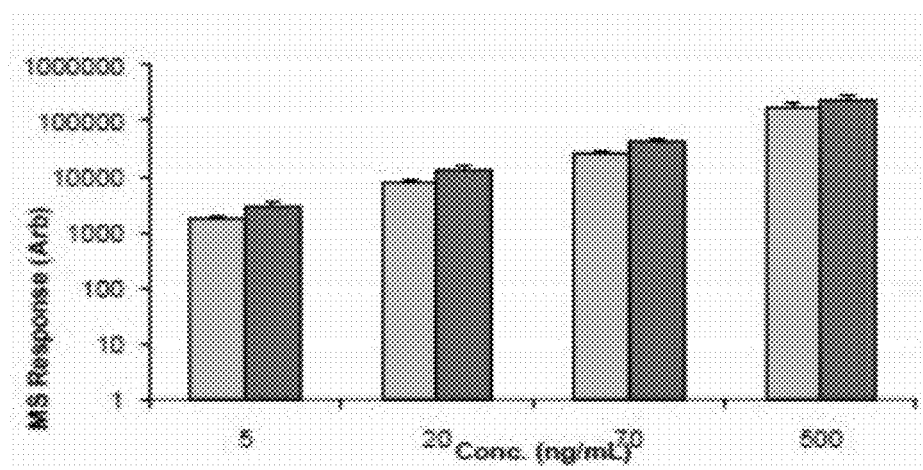
FIG. 2 is a graph showing the similarity of recoveries between sample dried at ambient and elevated temperature.

The SEM micrographs also allowed the macroporous structure of the material to be directly visualised. The micrographs show clearly the homogenous pore structure that can be achieved (FIG. 1). Covering the polymerization mixture with an unfunctionalised glass slide does not cause any significant damage to the surface of the monolith. As conformation, SEM images were obtained of the unfunctionalised glass cover plate (FIG. 2). This image clearly illustrates that the removal of the cover plate causes only marginal damage to the surface of the monolith.

The porous polymers may also include other additives such as rheology modifiers, fillers, tougheners, thermal or UV stabilizers, fire retardants, lubricants, surface active agents. The additive(s) are usually present in an amount of less than about 10% based on the total weight of the activation treatment or the combination of solvent(s), agent(s) and additive(s). Examples include:

(a) rheology modifiers such as hydroxypropyl methyl cellulose (e.g. Methocell 311, Dow), modified urea (e.g. Byk 411, 410) and polyhydroxycarboxylic acid amides (e.g. Byk 405);

(b) film formers such as esters of dicarboxylic acid (e.g. Lusolvan FBH, BASF) and glycol ethers (e.g. Dowanol, Dow);

(c) wetting agents such as fluorochemical surfactants (e.g. 3M Fluorad) and polyether modified poly-dimethyl-siloxane (e.g. Byk 307, 333);

(d) surfactants such as fatty acid derivatives (e.g. Bermadol SPS 2543, Akzo) and quaternary ammonium salts;

(e) dispersants such as non-ionic surfactants based on primary alcohols (e.g. Merpol 4481, Dupont) and alkylphenol-formaldehyde-bisulfide condensates (e.g. Clariants 1494);

(f) anti foaming agents;

(g) anti corrosion reagents such as phosphate esters (e.g. ADD APT, Anticor C6), alkylammonium salt of (2-benzothiazolythio) succinic acid (e.g. Irgacor 153 CIBA) and triazine dithiols;

(h) stabilizers such as benzimidazole derivatives (e.g. Bayer, Preventol BCM, biocidal film protection);

(i) leveling agents such as fluorocarbon-modified polymers (e.g. EFKA 3777);

(j) pigments or dyes such as fluorescents (Royale Pigment and chemicals);

(k) organic and inorganic dyes such as fluoroscein; and (l) Lewis acids such as lithium chloride, zinc chloride, strontium chloride, calcium chloride and aluminum chloride.

(m) Suitable flame retardants which retard flame propagation, heat release and/or smoke generation which may be added singularly or optionally include:

Phosphorus derivatives such as molecules containing phosphate, polyphosphate, phosphites, phosphazine and phosphine functional groups, for example, melamine phosphate, dimelamine phosphate, melamine polyphosphate, ammonia phosphate, ammonia polyphosphate, pentaerythritol phosphate, melamine phosphite and triphenyl phosphine.

Nitrogen containing derivatives such as melamine, melamine cyanurate, melamine phthalate, melamine phthalimide, melam, melem, melon, melam cyanurate, melem cyanurate, melon cyanurate, hexamethylene tetraamine, imidazole, adenine, guanine, cytosine and thymine.

Molecules containing borate functional groups such as ammonia borate and zinc borate.

Molecules containing two or more alcohol groups such as pentaerythritol, polyethylene alcohol, polyglycols and carbohydrates, for example, glucose, sucrose and starch.

Molecules which endothermically release non-combustible decomposition gases, such as, metal hydroxides, for example, magnesium hydroxide and aluminum hydroxide.

Expandable graphite

Preparation, Storage and Analysis of Body Fluids

The porous polymer monoliths described herein are used for storing body fluids, particularly blood and blood plasma for future analysis (e.g. of analytes including pharmaceutical agents or metabolites thereof). Blood or blood plasma samples can be applied directly to the porous polymer monoliths. The combination of sample and monolith are then dried to form a solidified sample that is adsorbed or adhered to the storage medium.

The body fluid sample typically comprises genetic material (e.g. DNA and RNA) and may be obtained from any source, for example, physiological/pathological body liquids (e.g., blood, urine, secretions, excretions, exudates and transudates) or cell suspensions (e.g., blood, lymph, synovial fluid, semen, saliva containing buccal cells).

The porous polymer monoliths provide for storage or subsequent analysis of a stored sample. The porous polymer monoliths can be composed of a solid matrix comprising functionality, and/or a composition or one or more active agents, which can protect against degradation of genetic material stored on the porous polymer monoliths or facilitate inactivation of microorganisms (e.g. microorganisms associated with a sample which may degrade the sample or may be potentially pathogenic to human handlers), facilitate the extraction of particular analytes, or facilitate matrix elimination to aid identification and analysis of analytes.

Dried body fluid samples on the porous polymer monoliths can be analysed at a later stage, for example used for pharmacokinetic analysis of pharmaceutical agents present in blood and plasma samples. Following drying of body fluid samples on the porous polymer monoliths, they are particularly suitable for storage and transportation of such samples, particularly whole blood and plasma samples, because at this stage they are considered to be relatively safe to handle and not infectious (e.g. with respect to infections diseases that may be carried in the blood such as HIV).

Long Term Storage

The porous polymer monoliths may be configured or adapted to enable storage of body fluids for many years, including the following time periods at least a day, a week, a month, 6 months, one year, two years, 5 years, 10 years, 20 years, or up to 50 years or more.

In an embodiment, the long term storage of a body fluid on the porous polymer monoliths can be facilitated by encasing the porous polymer monoliths in a protective material, for example a plastics material such as polystyrene, which can be subsequently removed when access to the stored sample is required.

In the storage of blood, the blood sample can be applied as a blood spot to the porous polymer monoliths. Functionality, components, or one or more agents, may be added to or incorporated into the porous polymer monoliths to provide particular optional properties suited for various purposes (e.g. for denaturing proteins, eliminating matrix or reducing or removing any pathogenic organisms in the sample). At the same time, the blood (and genetic material and/or analytes therein) can be protected from degradation factors and processes so that the relatively stable dried blood sample can then be stored and transported to a diagnostic laboratory. The analytes or genetic material can be extracted, analysed or used in situ on the porous polymer monoliths.

Active agents or a composition used with the porous polymer monoliths can comprise, for example, a monovalent weak base (such as "Tris", tris-hydroxymethyl methane, either as the free base or as the carbonate), a chelating agent (such as EDTA, ethylene diamine tetracetic acid), an anionic detergent (such as SDS, sodium dodecyl sulphate), guanidine, or uric acid or a urate salt. Other agents may include retaining agents to reduce the loss of analytes in subsequent analysis, which may occur during storage or pre-analysis treatment procedures.

Monomers with specific functionality can be incorporated to aid the elimination of the biological matrix from the sample. The ability to functionalise the surface of the paper based medium is limited, whilst simple protocols for the modification of polymeric monolithic media to incorporate functionality are well established.

In another embodiment, functionality can be incorporated into the porous polymer monolith for in situ elimination of undesirable components in blood that impede the detection of specific analytes, for example pharmaceutical agents or other low or small molecular weight compounds. In one particular embodiment, the surface area of the porous polymer monolith can be provided with ion exchange properties to facilitate the adherence thereon of selected pharmaceutical agents or non-adherence of selected contaminants present in the body fluid. The porous polymer monolith may therefore be used to analyse body fluids dried thereon without the need for chemical based pre-treatment. In another particular embodiment, the ion exchange properties may be provided by functional groups present on a monomer or co-monomer from which the porous polymer matrix is formed, and/or a post polymerisation surface modification comprising co-polymerisation grafting or other chemical modification.

In one embodiment, prior to a blood sample being adsorbed or adhered to the medium, the blood sample can be lysed to facilitate adherence of the sample to the medium. In an alternative embodiment, the pore size of the porous polymer monolith medium can be provided to be at or above the diameter of red blood cells (typically about 6,000 to 8,000 nm) to facilitate adherence of the blood sample to the medium.

In an embodiment, there is provided a method of storing a body fluid for future analysis comprising applying a body fluid sample to a porous polymer monolith medium and drying the body fluid such that the sample at least partially solidifies and adsorbs or adheres to the porous polymer monolith medium.

In another embodiment, a method of storing a body fluid for future analysis can comprise:

applying one or more body fluid samples to one or more regions of the porous polymer monolith medium;

partially drying the one or more samples applied to the medium;

separating any one or more regions of the porous polymer monolith having sample applied thereto from regions without sample applied thereto;

further drying the one or more samples applied to the one or more regions of the medium; and storing the one or more samples applied to the one or more regions of the medium.

The separating of any one or more regions of the porous polymer monolith having sample applied thereto from regions without sample applied thereto, may comprise substantially removing any medium not having body fluid applied thereto from around the sample, for example trimming or cutting away medium at or near the perimeter of the sample. The medium may be trimmed or cut away from around the sample such that the sample substantially covers the surface of the region to which the sample was applied, for example by using a hole punch of narrower diameter than a blood spot sample. In other words, the blood spot sample can extend at or near to the outer edge of the porous polymer monolith medium region to which the sample is applied. One advantage of this embodiment is that cracking of the sample can be reduced or prevented during the drying of the sample. The removal of any medium that is not contacted by the sample can facilitate adherence and non-cracking of the sample upon drying. Typically the sample is cut away or punched out from excess medium.

The samples applied to the medium are typically between about 5 and 10 mm in diameter, for example generally spherical and of a size of 10 to 100 mm$^2$. For example, the one or more samples can be selected from any one of the following sizes (mm$^2$) 1, 10, 20, 30, 40, 50, 60, 70, 80, 90, or 100. In another embodiment, the one or more regions can be selected from any one of the following sizes (mm$^2$) 1, 10, 20, 30, 40, 50, 60, 70, 80, 90, or 100. It will be appreciated that depending on the procedure, application or equipment used, variability may be associated with the application of samples to the medium, and ranges above, below or between these sizes also fall within the scope of the invention. The medium can also be sized or shaped to facilitate the substantial coverage of its surface with a body fluid sample, for example by providing one or more individual regions of the medium on a support material (e.g. an array), the regions being of a size that enables application of a sample thereto that can cover the surface thereof. Various patterns and arrangements of one or more samples to one or more regions also fall within the scope of these embodiments. For example, an array of body fluid samples can be applied to the medium, such as by providing an individually separated array of 5×5 samples of about 20 mm$^2$. In another embodiment, the array of samples may be applied to and/or cut away from a single medium, or applied to an array of one or more individual regions of medium.

In an embodiment, the drying of the body fluid, such as blood or blood plasma, is enhanced by application of at least one of elevated temperature, forced convection or reduced pressure. The elevated temperature may be in a temperature range above ambient but below the temperature at which the integrity of storage medium or sample is compromised. In a particular embodiment the elevated temperature is in the range between 30 and 150° C., 40 and 120° C., and more particularly between about 60 and 100° C., or 30° C. and above, 50° C. and above, 70° C. and above, 90° C. and above, 110° C. and above, or 130° C. and above. In one particular embodiment the elevated temperature is above about 90° C., which for certain types of monolith mediums and samples may enhance future analysis of the samples or prevent cracking of the samples upon drying. Typically the samples can be dried in about 10 to 20 minutes under the elevated temperatures. In a particular embodiment, the reduced pressure is in the range of 5 to 760 mmHg. Reduced pressure can be applied by way of vacuum apparatus.

There is also provided a method of analysis involving the identification and detection of an analyte from a stored body fluid sample adsorbed or adhered to a porous polymer monolith medium.

In one embodiment, the stored body fluid sample can be analysed without pre-treatment and/or removal from the porous polymer monolith medium. In other words, the samples stored on the monolith mediums can be used directly in analysis without further modification. The analytes can include small molecules and low molecular weight compounds present in blood or blood plasma samples, for example, pharmaceutical agents including new chemical entities (NCEs) and any metabolites thereof, peptides, proteins, oligonucleotides, oligosaccharides, lipids or other labile compounds. In another embodiment, the analysis involves the simultaneous analysis of at least two analytes. In a particular embodiment, the at least two analytes comprise an NCE and a metabolite thereof.

Porous Polymer Monoliths for Selective Extraction and Matrix Elimination

The incorporation of ion-exchange functionality into the porous polymer monoliths was investigated to facilitate selective extraction of particular analytes, such as pharmaceutical agents or NCEs, and to facilitate matrix elimination. Both co-polymerization and surface modification techniques were employed to incorporate functionality into the polymer monoliths.

Typically the porous polymer monoliths have a hydrophilic surface to facilitate adsorption of the body fluid. Functionality that can be incorporated into the porous polymer monoliths to facilitate in situ sample cleanup or matrix elimination, facilitate specific extraction (e.g. of analytes), or facilitate bioanalysis. Strong cation exchange (SCX) functionality may be provided, for example, by incorporating sulphonic acid type surface groups (e.g. HEMA-co-SPMA), weak cation exchange (WCX) functionality may be provided by carboxylic acid surface groups, strong anion exchange (SAX) may be provided by quaternary amine surface groups, and weak anion exchange (WAX) may be provided by tertiary amine surface groups.

Solid phase extraction (SPE) methods involve sample preparation to purify and concentrate analytes from a matrix by the sorption onto a medium followed by the elution with an appropriate solvent. The analyte partitions between the solid phase and the solvent and only those analytes with a high affinity for the solid phase are retained. Following matrix elimination the analyte can then be eluted from the solid phase and analysed.

Polymer monoliths with acidic functional groups can be fabricated for the selective extraction of NCEs containing basic functional groups while polymer monoliths with basic functionality allow the selective extraction of NCEs that are somewhat acidic. The incorporation of functionality into porous polymeric monoliths is generally well established and can be achieved using several different strategies.

Two possible methods for the incorporation of specific functionalities into the porous polymeric monolithic medium are either by incorporation of a functional monomer directly into the polymerization mixture or by a post-polymerization of the monolithic scaffold. The approach of introducing the functional monomer directly into the polymerization mixture along with the structural monomers is by far the simplest approach as no subsequent modifications are required. However, as the functional monomer is part of the polymerization mixture it is possible that a large portion of the ionisable groups will be trapped within the bulk of the media and not available at the surface of the monolith for interaction with the NCE.

The second approach is a post-polymerization reaction which imparts the functional groups directly to the surface of the monomer by covalent attachment. The monolithic scaffold can be optimized separately meaning that a variety of functionalities can be imparted onto the same monolithic scaffold. The advantage of employing a post polymerization reaction is that the functionality is imparted directly onto the surface of the monolith meaning that it is easier to synthesise higher capacity materials for increased sample loading. Surface functionality can be imparted using two very different approaches; the first is an alternation of the surface chemistry though a chemical reaction. This approach requires the structural monomers to include reactive groups. The second option is to complete a second polymerization reaction on top of the supporting monolithic scaffold; this technique is known as surface grafting.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Experimental

1. Equipment

The macroporous structure of all monoliths was measured by mercury intrusion porosimetry using a Micromeritics AutoPore IV 9505 (Norcross, Ga., USA) porosimeter. Specific surface area was determined by the Brunauer-Emmet-Teller (BET) [Brunauer S et al, *Journal of the American Chemical Society*, 1938. 60: p. 309-319] method using a Micromeritics TriStar II 3020 automated nitrogen sorption/desorption instrument. All monoliths were degassed in a Micromeritics at a temperature of 50° C. for 24 hours.

An OAI LS30/5 Deep UV irradiation system (San José, Calif., USA) with a 500 W HgXelamp was utilised for all UV exposures. Lamp calibration to 20.0 mW/cm$^2$ was performed with an OAI Model 306 intensity meter with a 260 nm probe head.

Scanning electron micrographs were obtained using an FEI Quanta 6000 Scanning Electron Microscope (FEI, Hillsboro, Oreg., USA) operated in low vacuum mode with an acceleration voltage of 15 to 30 kV.

All LC-MS/MS analysis was performed using an Aglient Technologies Liquid Chromatograph (Agilent Technologies, Waldbronn, Germany) equipped with an API400 Triple Quadrapole mass spectrometer (Applied Biosystems Sciex Instruments, Foster City, Calif., USA) and Applied Biosystems Analyst® 1.4.2 software. Ionisation was using atmospheric pressure chemical ionization (APCI). A CTC PAL Autosampler (Leap Technologies, Carrboro, N.C., USA) was employed for all injections, with a constant temperature of 4° C. An Onyx C18 monolithic column was employed (3.00×100 mm) (Phenomenex, Macclesfield Cheshire, UK) and the temperature was held constant at 40° C.

Cation-exchange capacity measurements were determined using a Dionex ICS1000 Ion Chromatography system (Sunnyvale, Calif., USA) equipped with suppressed conductivity detection and a 25 µL sample loop. An IonPac CSI2A cation exchange column (5×250 mm) was employed. Anion-exchange capacities were determined using a Dionex DX600 system equipped with suppressed conductivity detection and a 25 µL sample loop. An IonPac AS18 anion exchange column (4×250 mm) was employed.

All methacrylate monomers were purified by filtration through a column of inhibitor remover beads (Aldrich) to remove the inhibitors; monomethyl ether hydroquinone and hydroquinone. The purified monomers were then stored in the freezer at −4° C.

2. Preparation of Monolith DBS Storage Medium a. Surface Modification of Glass Slides Corning glass microscope slides (75×50 mm, 0.96 to 1.06 mm thick, Ted Pella Inc, Calif., USA) were activated with 0.2 mol/L NaOH for 1 hour with agitation (Gyro-Rocker 9, Stone, UK), then rinsed with water until the pH on surface of the glass slide measured neutral. These were then washed with 0.2 mol/L HCl for 1 hour with agitation, rinsed with water and dried at 60° C. for 1 hour. A 20% (w/w) solution of 3-(trimethoxysilyl) propyl methacrylate in 95% ethanol adjusted to pH 5 using acetic acid was employed to achieve surface vinylisation with the solution sandwiched between two plates for 1 hr. Modified slides were then washed with acetone and dried under vacuum at room temperature for 12 hours.

b. Preparation of Mould for Medium Fabrication

The preparation of the mould to encase the polymerization mixture involved adhering a piece of Teflon (500 µm thick) onto a glass microscope slide with a generic epoxy resin. An activated glass slide was then placed on top of the structure for the monolith to adhere too. The mould was clamped with bulldog clips.

c. Preparation of Flat Polymeric Monolithic Sheets

The polymerization mixture for the synthesis of poly(2-hydroxyethyl methacrylate-co-ethylene glycol dimethacrylate) monoliths was prepared in 5.0 g quantities by combining the appropriate reagents in a 20 mL screw top vial. Typically the polymerization mixture was composed of 24% HEMA, 16% EDMA, 20% cyclohexanol, 40% 1-dodecanol and 1% (all w/w) DMPAP with respect to the monomers.

The following process for polymerization was employed for each of the monolithic sheets. This mixture was shaken and sonicated for 2 minutes, then deaerated by purging with high purity $N_2$ for 10 minutes. The mixture was then transferred to the mould using a Pasteur pipette and exposed to UV light for 900 seconds. After this, the mould was disassembled and the affixed monolith was rinsed in a bath of methanol with agitation for at least 10 hours to remove residual monomers and porogens. Finally the monolith was left to dry overnight in a vacuum oven at room temperature. Median pore diameters were relatively constant at about 600 nm for monoliths produced using 35-45% dodecanol in the porogen composition, where 100% dodecanol provided a median pore size of about 400 nm.

3. Preparation of Functionalised DBS Medium a. Weak Cation-Exchange (WCX) Functionality A co-polymerization procedure for the poly(ethylene glycol dimethacrylate-comethacrylic acid) monoliths in the form of flat sheets was conducted. The polymerization mixture was prepared in 5.0 g quantities, containing 8.12% MAA, 20.3% EDMA, 47.4% 1-decanol, 27.3% (all w/w) 1,4 butane diol. Approximately 1% (w/w) DMPAP, was incorporated with respect to the total monomers.

Another WCE produced=poly (GMA-co-EDMA) median pore size found to be 340-360 nm for porogen compositions comprising 40-45% dodecanol and about 385 nm for 100% dodecanol.

Another suitable functional monomer employed for WCX is acylic acid (AAc).

b. Strong Cation-Exchange (SCX) Functionality

Mixed mode strong cation-exchange/polar poly(2-hydroxyl ethyl methacrylate-coethylene glycol dimethacrylate-co-3-sulfopropyl methacrylate) monoliths (MSCX) were prepared as follows. An aqueous solution of SPMA was prepared by dissolving 0.1 g of SPMA potassium salt in 3 mL of water. The polymerization mixture was prepared in 5.0 g quantities containing 24% HEMA, 16% EDMA and 6% (all w/w) of the aqueous SPMA solution. The porogenic solvents employed were 43.2% 1-decanol and 10.8% 1,4 butane diol, and 1% (all w/w) of DMPAP with respect to the monomers.

Poly(glycidyl methacrylate-co-diethylene glycol dimethacrylate) monoliths were prepared as a monolithic scaffold for the strong cation-exchange (SCX) monoliths. The polymerization mixture was prepared in 5.0 g quantities with 50% GMA, 50% DEGMA, 36% 1-dodecanol, 24% cyclohexanol and 1% (all w/w) DMPAP with respect to the monomers.

The surface modification reaction was completed by submerging the dry material in bath of aqueous modification solution containing 1 mol/L $Na_2SO_3$. The sulfonation reaction was allowed to proceed in a 75° C. oven (Barloworld Scientific, Hope Valley, England) for 12 hours with periodic shaking at hourly intervals. The material was then rinsed by submerging in a bath of 10 mmol/L $HNO_3$ for 1 hour and finally washed in water for at least 24 hours.

Another suitable functional monomer employed for SCX is acrylamido-2-methylpropane sulfonic acid (AMPS).

c. Weak Anion-Exchange (WAX) Functionality

The poly(GMA-co-EDMA) monolith described above was utilised as the scaffold for the weak anion-exchange (WAX) monolith. The surface modification was completed by submerging the dry monolith in a bath of the modification solution containing 20 mmol/L $Na_2CO_3$, 17 mmol/L diethylamine, and 3 mmol/L NaCl. The reaction was left to proceed for 8 hours at 60° C. with agitation at hourly intervals. The monolith washed for 3 hours with water and finally washed with methanol 1 hour. The monolith was then dried under vacuum.

Another suitable functional monomer employed for WAX is dimethayl amino ethyl methactylate (DMAEM).

d. Strong Anion-Exchange (SAX) Functionality

The poly(HEMA-co-EDMA) material was the support scaffold for the strong-anion exchange (SAX) monolith based on the grafting methodology to form flat sheets. The grafting mixture contained 15% methacryloyloxyethyl trimethylammonium chloride, and 1% (both w/w) of the photoinitiator benzophenone with respect to the functional monomer in a 3:1 v/v solution of t-butanol and $H_2O$. This solution was prepared immediately prior to use. The dry material was submerged in a bath of the grafting mixture for 30 minutes with continual agitation. The material was covered with a glass slide of the same dimensions and clamped with bulldog clips. The material was exposed to UV light for 180 seconds. The material was rinsed in an agitated bath of methanol for at 3 hours with to remove any unreacted grafting solution thus avoiding a continuation of the free-radical polymerization.

To optimise the grafting method the exposure time was investigated. Methodology employed to introduce the functional monomer was changed, it involved preparing 2.5 mL of grafting mixture which contains 15% functional monomer in 3:1 v/v t-butanol:water and 1% of the benzophenone. The mixture was pippetted over the surface of the monolithic scaffold (polyHEMA-co-EDMA) and left for 5 mins. Following a quartz slide was used to cover the monolith, the quartz was clamped on with bulldog clips. This was then irradiated for 2, 5, 10, 20, 40 and 80 minutes. The monomer methacryloyloxyethyltrimethylammonium chloride (META) was employed for the method development. The percentage of nitrogen on each of the grafted monomers could be determined by flash elemental analysis, which was identified to be about 0.1% N for 1-2 minutes exposure time, about 0.4% N for 20 minutes exposure time, and about 0.5% N for 80 minutes exposure time. Blood and plasma spotted onto each of the exposed materials was found to penetrate sorbents when the material had been exposed for less than 40 min, suitably about 20 mins.

4. Monolith Characterization a. Characterization of Bulk Porous Polymeric Monolithic Sheet All fabricated monolithic materials were inspected visually. A 15 µL sample of whole human blood was then spotted onto the material and the adsorption, spreading and any chromatographic effects were noted. Mercury intrusion porosimetry was performed using approximately 100 mg of sample analyzed in a powder penetrometer. The specific surface areas of approximately 100 mg of sample were calculated by the nitrogen adsorption/desorption isotherms. The morphology of the monoliths was directly imaged by scanning electron micrograph (SEM).

b. Ion-Exchange Capacity

The cation-exchange monoliths were pretreated by submerging them in an agitated bath of 0.5 mol/L HCl for 12 hours. The monoliths were then washed in an agitated bath of water for 12 hours with periodical water changes at hourly intervals for the first 4 hours. Samples were then dried under vacuum for 12 hours. Approximately 100 mg of sample was submerged in 10 mL of 100 mmol/L NaCl for 12 hours. The anion-exchange monoliths were submerged in a bath of 0.5 mol/L NaOH and the same pretreatment procedure outlined above was employed.

A four point calibration curve of NaCl was prepared with concentrations of 40, 60, 80 and 100 mM and measured by cation-exchange as well as anion-exchange chromatography. All samples were filtered with a 0.22 µm nylon membrane (Phenomenex, NSW, Australia) prior to analysis. For the cation analysis, a 35 mmol/L methanesulfonic acid eluent was employed at a flow rate of 1.0 mL/min, with a column temperature of 35° C. The 10 mL NaCl sample subjected to the SCX monolith was analysed to determine the reduced concentration of $Na+$. For anions, a 30 mmol/L KOH eluent was employed at a flow rate of 0.9 mL/min, with column temperature of 30° C. The 10 mL NaCl sample subjected to the anion-exchange monoliths was analysed to determine the reduced concentration of $Cl^-$.

A calibration curve of $Na_2CO_3$ was prepared using cation-exchange chromatography. Using $Na_2CO_3$ the same methodology was applied to determine the reduced concentration of $Na^+$ caused by exposure to the WCX.

5. Preparation of Calibrations and Quality Control Standards

Primary stock solutions of test pharmaceuticals were prepared in dimethyl sulfoxide at a concentration of 1 mg/mL. Working standards solutions were prepared from the primary stock solutions at 100, 100 and 1 μg/mL. Fluconazole, gabapentin and propranolol were prepared in an water:methanol (9:1 v/v) solution, while ibuprofen and maraviroc were prepared in a water:methanol (1:1 v/v) solution. UK 258 300 was prepared in an water:acetonitrile (1:1 v/v) solution. The internal standard (IS) for each analyte was prepared at 1 μg/mL in the appropriate aqueous solution.

Calibration standards were prepared by a dilution of the appropriate working solution in blood. Calibration standards were prepared on the day of analysis using rat blood or plasma at concentrations of 5, 10, 30, 50, 100, 200, 400, 800 and 1000 ng/mL. Quality control (QC) samples in rat blood or plasma were also prepared from the same working solutions at concentrations of 5, 20, 70 and 500 ng/mL. Homogeneity of samples was ensured by vigorous mixing.

6. Analytical Validation of Monolithic DBS Storage Medium a. Sample Processing

Fluconazole was employed to validate the poly(HEMA-co-EDMA) monolith with 15 μL aliquots of each calibration standard spotted directly onto the medium with an air displacement pipette. Eight replicates of each of the quality control samples were also spotted directly onto the material. Spots were left to adsorb for approximately 1 hour, after which a hole punch (Harris Unicore, Ted Pella, Calif., USA) was used to remove the entire blood spot from the bulk material. A 6 mm diameter hole punch was utilised for whole blood spots while the 7 mm diameter hole punch was utilised for plasma spots. Blood spots were placed in a 2 mL square well filter plate (Strata Impact Protein Precipitation Plate, Phenomenex, Cheshire, UK) for a further 1 hour to ensure that they were completely dried.

After this 300 mL of methanol containing 5 ng/mL fluconazole-D8 IS was added to each well. The fluconazole was extracted on a flat bed mixer (Heidolph Instruments, Kelheim, The Netherlands) at 1300 rpm for 30 minutes. Samples were filtered into a 2 mL 96 well polypropylene plate using a vacuum manifold system (Tomtec Inc, Hamden, Conn., USA). The filtrate was evaporated under a stream of nitrogen at 15° C. Samples were then reconstituted with 200 μL of water:methanol (9:1 v/v).

b. Accelerated Drying

Aliquots (15 μL) of the QC whole blood samples were spotted directly onto the poly(HEMA-co-EDMA) material in replicates of 4. Samples were then dried in a Polartherm Series 9000 oven (Sandra Selerity Technologies Inc. Salt Lake City, Utah, USA) at 100° C. for 10 minutes. Blood spots were punched out using a 6 mm diameter hole punch. The extraction of the fluconazole was completed using the same methodology described above.

c. Simultaneous Analysis

Fluconazole and propranolol were employed to validate the potential of simultaneous analysis. Samples in both whole blood and plasma were prepared as outlined above. Aliquots of each calibration standard were spotted directly onto the medium with an air displacement pipette. Four replicates of each of the quality control samples were also spotted directly onto the medium. Protocols for sample processing were conducted as described above. The IS employed for propranolol was mexiletine.

7. Development of Generic SPE Protocols a. WCX Monoliths and SAX Monoliths

The material was pretreated by submerging it in a bath containing 5% NH4OH, the bath was agitated periodically for 2 hours. The material was left to dry at ambient temperature for 3 hours. A 50 ng/mL of UK 258 300 sample was made up in whole blood, plasma and a water:methanol (9:1 v/v) solution from the 10 μg/mL stock solution.

Five spots of each solution were spotted directly on the WCX monolith; circles were drawn around the aqueous spot. Samples were left to dry at ambient temperature for 1 hour. The 6 mm, 7 mm and 8 mm diameter hole punch were used to punch out the blood, plasma and aqueous spots respectively. The spots were placed into individual wells of a 96 well plate and dried for a further 1 hour.

The method then involved providing 300 μL of the 5% NH$_4$OH wash solution containing 5 ng/mL of the IS UK 280 111 to each well, the 96 well block was placed on a flat bed mixer at 1300 rpm for 15 minutes. Each liquid sample was transferred to an individual well of a new 96 well plate. The same protocol was applied to a second wash of 300 μL of methanol containing 5 ng/mL of IS. Solutions of 1-5% formic acid in methanol were used to elute the analyte in successive order, each solution contained 5 ng/mL of the IS. Samples were evaporated to dryness with nitrogen and reconstituted with 500 μL of water:methanol (9:1 v/v). An identical procedure was repeated for the SAX monolith using the analyte ibuprofen and the IS ibuprofen-D$_3$.

b. SCX Monoliths and WAX Monoliths

The procedure was similar to the methodology described above. However, monoliths were pretreated with an aqueous solution containing 5% formic acid. Solutions of 1-5% NH$_4$OH in methanol were used to elute the analyte in successive order, each solution contained 5 ng/mL of the IS. The analyte employed for method development of the SCX was maraviroc with the IS maraviroc-D5 and gabapentin with the IS gabapentin-D4 for the WAX material.

8. Analytical Method Validation of Functionalized Monolithic Medium a. Sample Preparation Protocols Initial sample preparation protocols were identical to those described above. Punched blood spots were placed polypropylene 96 well plate for a further 1 hour to ensure that they were completely dried. The SCX and WAX monoliths were pretreated by submerging in a bath of 5% formic acid solution for 2 hours. The SAX monoliths were pretreated by submerging in a bath of 5% NH$_4$OH solution for 2 hours. Monoliths were dried at ambient temperature for 2 hours.

The method then involved using 300 mL of the 5% NH$_4$OH solution to wash the SAX material on a flat bed mixer at 1300 rpm for 30 mins. The solution was removed from the well and discarded. A further wash was completed with methanol on a flat bed mixer at 1300 rpm for 30 mins. The analyte was eluted with 5% formic acid in methanol containing 5 ng/mL IS. The acidic eluate was transferred to a separate 96 well plate and samples were evaporated under a stream of nitrogen. The sample was then reconstituted with 500 μL of water:methanol (9:1 v/v).

The protocols applied for SCX and WAX were similar to the methodology just described thus will not be described in detail. However, 300 mL of the 5% formic acid solution was used to wash the SCX and WAX material and the analyte was eluted with 5% formic acid in methanol containing 5 ng/mL of IS.

9. LC-MS/MS Experiments

Various chromatographic conditions were employed for each analysis methodology. The scan mode was multiple reaction monitoring (MRM), the precursor ion (M+1) m/z and after collision product ion were used for the quantification of the analytes. The MS was operated in the positive MRM mode for the analysis of fluconazole, propranolol, maraviroc and UK 258 300. For the analysis ibuprofen and gabapentin the MS was operated in negative MRM mode. The scanned MRM ion ranges employed for analyte quantification are given in Table 1.

TABLE 1

The scanned MRM ion ranges for analyte quantification

| Analyte | MRM1 (m/z) | MRM2 (m/z) | MRM IS (m/z) |
| --- | --- | --- | --- |
| Fluconazole | 307 to 238 | 307 to 220 | 315 to 244 |
| Propranolol | 260 to 116 | | 180 to 58 |
| Maraviroc | 514 to 389 | | 519 to 394 |
| UK 258 300 | 683 to 496 | 683 to 227 | 615 to 428 |

10. Modification of Porous Polymer Monoliths

A porogenic solvent such as a mixture of 1-dodecanol and cylcohexanol can be employed to modify the porous properties of the monolith. Varying the type and amounts of solvents can modify distribution of monoliths which can be examined by mercury intrusion porosimetry (MIP). HEMA is a polar monomer and increasing the concentration of the less polar porogen, such as 1-dodecanol, may result in monoliths with larger pores.

It was found that increasing the percentage of dodecanol between 38-100% of porogenic solvent in a mixture of dodecanol and cyclohexanol had no measurable effect and the pore size distribution remained constant: at approximately 600 nm. A binary porogenic solvent of methanol and hexane at equal ratios was employed to achieve large pores in the poly(HEMA-co-EDMA) monolith. The pore size distribution achieved was 7087 nm. Monoliths with smaller pore size were more reproducible, for example poly(HEMA-co-EDMA) monolith containing a binary porogenic solvent of 40% dodecanol and 20% cyclohexanol was developed as a potential sorbent for the storage of whole blood and plasma.

The visual appearance of the monolith is considered to be a reliable indicator of the pore size due to light scattering. The monoliths studied appeared chalky which indicated a macroporous material. Analysis by MIP confirmed this supposition, with the median pore diameter measured at 600.1 nm and the monolith porosity being 68%. The specific surface area for the monolith was determined by BET analysis.

The SEM micrographs allowed the macroporous structure of the material to be directly visualised. The micrographs show clearly the homogenous pore structure that can be achieved with this polymerization mixture (FIGS. 1a and 1b). Covering the polymerization mixture with an unfunctionalised glass slide does not cause any significant damage to the surface of the monolith. As conformation, SEM images were obtained of the unfunctionalised glass cover plate (FIG. 2). This image clearly illustrates that the removal of the cover plate causes only marginal damage to the surface of the monolith.

11. Investigation into the Potential of Whole Blood and Plasma Storage

To investigate the potential of the poly(HEMA-co-EDMA) monolith as a medium or sorbent for the storage of whole blood and plasma samples 15 µL aliquot of whole human blood and plasma were spotted directly onto the monolith. Both the blood and plasma samples penetrated the entire 500 µm thickness of the sorbent and an excellent uniformity was displayed for both spot size and shape. Furthermore, the plasma samples completely dried on this monolithic sorbent. Dimensional analysis was performed for both DBS and DPS (n=6), the approximate size of blood spots was 6 mm in diameter while for plasma spots were approximately 7 mm in diameter.

Unfortunately, when the whole blood sample dried on the sorbent the monolith displayed cracking within the confines of spot. This cracking was not replicated within the plasma spots. Therefore the formulated hypothesis was that the cracking correlated with the presence of the cellular debris. This theory was considered reasonable as the median pore diameter of the poly(HEMA-co-EDMA) monolith was approximately 600 nm, which is significantly smaller than the implicit size of the red blood cells (RBC). It could be seen that the RBC's pool on the surface of the sorbent and it is believed their presence imparts physical stress on the monolith which causes it to crack.

Further evidence to support this hypothesis followed when a sample of whole blood containing physically lysed RBC was applied to the sorbent. Visually the monoliths displayed a significant reduction in cracking. Thus the fabrication of a polymer monolith containing macropores larger than the RBCs was regarded as preferred. A binary porogenic solvent containing methanol and hexane afforded a pore size of approximately 7.0 µm. Aliquots of whole blood were spotted onto this sorbent, the blood sample penetrated the entire thickness of this sorbent and no RBC pooling was displayed on the surface of the monolith. Despite this the sorbent still displayed a substantial degree of cracking when the blood sample dried.

Fortunately, the cracking of the monolith could be eliminated completely by simply using a hole punch to remove the sample disk from the bulk material. Cracking was reasoned to occur as the sorbent material expands slightly when wet and consequently shrinks when dry. This occurs within the confines of the bulk monolith and subsequently results in a physical stress that causes cracking. While the cracking of the monolith may not affect the recovery of analytes from the sorbent it imparts some sample handling difficulties and also means that the whole blood spot must be sampled to maintain analytical validity.

The polymer monolith sample disks, at least in particular embodiments, can provide a volumetric measurement comparable to liquid measurements, particularly as sample disks can easily and cleanly be removed from the bulk of the monolith.

12. Analytical Validation of Monoliths for DBS a) Testing Details and Analysis

Having fabricated a suitable monolith to act as a sorbent for whole blood which allows for the simplified storage and transportation of samples, the monoliths were further tested to validate analysis of samples following storage. The novel technology was validated in accordance with the Guidance for Industry (2001: Rockville). The fundamental parameters for bioanalytical method development are accuracy, precision, selectivity, sensitivity and stability. The commercialized pharmaceutical drug fluconazole was employed to determine the accuracy, precision and sensitivity of the drug recoveries from the monolithic sorbent. The selectivity and stability of fluconazole in whole blood or plasma was excluded in the present study as both are well established.

The analyte fluconazole could be successfully extracted from the monolithic sorbent using the organic solvent methanol. A calibration plot of the analyte/internal standard peak ratio (peak area ratio) versus the nominal concentration of fluconazole was constructed with the lower limit of quantification (LLOQ) being 5 ng/mL. An excellent linear response, r2=0.998, was observed for the recoveries from whole blood sample over the range of 5-1000 ng/mL.

Consequently, this calibration curve was employed to determine the inter-assay accuracy and precision of the monolithic sorbent using eight replicates at of each of the four QC standards. Accuracy was determined by calculating the percent deviation from the nominal concentration and the precision was determined by the percent of variation in each replicate set.

The Guidelines for Industry state that the mean value for accuracy of an analytical method should be within 15% of the actual value except for LLOQ where it should not deviate by more than 20%. The guidelines further state that the precision should not exceed 15% of the coeffficent variation and the LLOQ which should not exceed 20%. The accuracy and precision data obtained from the fluconazole results are displayed in Table 2 and all accuracies and precisions fulfilled the required criteria.

TABLE 2

The inter-assay accuracy and precision for fluconzole in whole rat blood recovered from a monolithic sorbent

| Nominal Concentration (ng/mL) | Mean Calculated Concentration (ng/mL) | Standard Deviation | Accuracy (%) | Precision (%) |
| --- | --- | --- | --- | --- |
| 5 | 5.69 | 0.27 | 114 | 4.70 |
| 20 | 21.23 | 1.45 | 106 | 6.81 |
| 70 | 65.85 | 11.35 | 94 | 17.24 |
| 500 | 492.00 | 31.39 | 98 | 6.38 |

Established DBS procedures were employed for a cross-validation with the data obtained from the paper based material which serves as a reference for the novel comparator technology. The accuracy and precision data for the fluconazole recoveries on the paper based media can be seen in Table 3. These values are directly comparable to the recoveries obtained from the monolithic sorbent and it can be seen that there is no significant difference in the performance of the two sorbents.

TABLE 3

The inter-assay accuracy and precision for fluconzole in whole rat blood recovered from a paper sorbent

| Nominal Concentration (ng/mL) | Mean Calculated Concentration (ng/mL) | Standard Deviation | Accuracy (%) | Precision (%) |
| --- | --- | --- | --- | --- |
| 5 | 5.1 | 0.38 | 102 | 7.49 |
| 20 | 17.5 | 1.64 | 116 | 9.35 |
| 70 | 74.8 | 2.76 | 107 | 3.69 |
| 500 | 522.5 | 11.78 | 104 | 2.25 |

However, monolith sorbent affords a large advantage over the paper sorbent as the analyte can be extracted from the sorbent while the biological matrix remains affixed. The biological matrix is eluted from the paper sorbent with analyte extraction and thus the sample must be further prepared prior to analysis, typically well established SPE protocols are employed.

Having confirmed that monoliths are a valid sorbent for the extraction of analytes from whole blood the potential to employ the technology to plasma samples was investigated. Again the analyte fluconazole was successfully extracted from the monolithic sorbent using methanol while the plasma sample remained affixed. A calibration plot of peak area ratio versus the nominal concentration of fluconazole was constructed with a 5 ng/mL LLOQ. The calibration curve exhibited a linear response of r2=0.996. The calibration curve was used to determine the inter-assay accuracy and precision (n=4) of the monolithic sorbent for plasma samples (Table 4).

TABLE 4

The inter-assay accuracy and precision for fluconzole in rat plasma recovered from a monolithic sorbent

| Nominal Concentration (ng/mL) | Mean Calculated Concentration (ng/mL) | Standard Deviation | Accuracy (%) | Precision (%) |
| --- | --- | --- | --- | --- |
| 30 | 25.70 | 1.82 | 86 | 7 |
| 100 | 105.28 | 9.59 | 105 | 9 |
| 400 | 463.00 | 58.46 | 116 | 13 |
| 800 | 884.25 | 26.21 | 111 | 3 |

The LLOQ was significantly higher for the plasma samples as there was not enough replicates to achieve meaningful results at the lower levels. However, again the accuracies and precisions adhered with the criteria for to validate the technology.

b) Potential for Simultaneous Quantification

Simultaneous analysis affords the advantage that both NCEs and their respective metabolites can be quantified simultaneously. Therefore the amount of sampling collection and sample preparation needed for ADME analysis can be reduced. Offering the potential of high through put analysis of NCEs and furthermore reduces the testing of preclinical species. The potential for simultaneous quantification of analytes was investigated with two commercialized pharmaceutical drugs, fluconazole and propranolol.

The two analytes were successfully recovered from the monolithic sorbent again using methanol. The calibration curve were linear over a concentration range of 5 ng/mL to 800 ng/mL for both the fluconazole and propranolol, with correlation coefficients of $r^2$=0.998 and 0.997 respectively for fluconazole and propranolol. The inter-assay performance for fluconazole and propranolol in dried rat blood are summarized in Table 5.

TABLE 5

The inter-assay accuracy and precision for fluconzole and propranolol in whole rat blood recovered from a monolithic sorbent

| Compound | Nominal Conc. (ng/mL) | Mean Calculated Conc. (ng/mL) | Accuracy (%) | Precision (%) |
| --- | --- | --- | --- | --- |
| Fluconazole | 5 | 6.16 | 123 | 29 |
| | 20 | 18.60 | 93 | 4 |
| | 70 | 83.38 | 119 | 9 |
| | 500 | 500.25 | 100 | 29 |
| Propranolol | 5 | 8.30 | 166 | 40 |
| | 20 | 17.80 | 89 | 3 |
| | 70 | 78.78 | 113 | 8 |
| | 500 | 535.00 | 107 | 18 |

The accuracies and precisions obtained did not comply with the assigned criteria. However, there was not enough replicates to conclusively determine that the monolithic sorbent was not suitable for simultaneous analysis. Rather these results strongly suggest the simultaneous analysis is quite possible.

c) Accelerated Drying Techniques

A significant disadvantage of employing the paper sorbent for DBS sampling is that accelerated drying cannot be employed to reduce the time required for sample preparation. Samples must be completely dried at ambient temperature which typically requires two hours.

To investigate the potential of implementing accelerated drying techniques to the monolithic sorbent, high temperatures were employed. The sample was placed in a generic oven at 100° C. until the sample was completely dried which required less than 10 minutes. The application of high temperature to accelerate the drying of the sample on the monolithic sorbent had a further advantage in that the DBS spots did not display cracking when dried above 90° C. The recoveries of the analyte, fluconazole, in samples dried at elevated temperatures were compared to the analyte recovery of samples dried at ambient temperatures (FIG. 2). The increase in sensitivity observed was reasoned to be due to complete RBC lysis meaning that any of the analyte that had partitioned into the RBC was able to be quantified.

13. Selective Extraction and Matrix Elimination a) Background Details

Generally, LC-MS/MS is employed for the bioanalytical analysis of NCEs as it affords both a high sensitivity and selectivity with short analysis times. Unfortunately, the sensitivity of the LC-MS/MS can be reduced due to suppression of the analyte response during ionization caused by the preferential ionization of interfering, non-volatile matrix components. Thus good sample preparation protocols are required to selectively extract the target analyte from biological matrices. One of the major drawbacks of paper based sorbents implemented for DBS sampling is that paper affords limited scope for functionalisation, therefore an additional extraction processes must be employed for matrix removal after the DBS sample has been eluted from the paper.

Established SPE techniques reduce the presence of matrix components responsible for ion suppression during MS/MS detection by selectively binding the NCEs to the sorbent and eluting the matrix components with a series of washes. Various materials can be utilized as sorbents for SPE; these include both porous and non-porous packed silica and polymer particles as well as agarose gels, dextrans and porous monoliths. The selective extraction is ensured by the incorporation of functionality into the sorbents. Acidic functional groups afford the selective extraction of basic NCEs while basic functionality allows the selective extraction of acidic NCEs. Porous polymer monoliths are particularly advantageous to the pharmaceutical industry as they can be fabricated in disk format and 96 of these disks can be bundled together in block manifold with the dimensions of a 96-well microtitre plate. This format can be fully automated meaning that more than one sample can be prepared at a time.

Porous polymer monoliths can be in the form of silica monoliths or polymer monoliths. Polymer monoliths afford the advantage of straightforward in situ fabrication and the porous structure allows for high permeability for the eluting solvents. Functionality can be imparted into the monolith using established and relatively uncomplicated techniques.

In situ co-polymerization is the simplest approach to impart functionality into a porous polymer monolith. It involves the incorporation of the functional monomer into the polymerization mixture. For example, an approach includes the photoinitated polymerization of a weak cation-exchange (WCX) monolith for the in-line SPE in capillary format utilizing the functional monomer methacrylic acid. Another approach can use the incorporation of the functional monomer sulfopropyl methacrylate can be used to achieve a mixed mode strong cation exchange (MSCX) monolith. However, the disadvantage of this simple approach is that the monolith typically affords a low ion exchange capacity as the functional groups become incorporated within the bulk polymer and cannot all contribute to the surface charge.

The ion-exchange capacity can be improved by increasing the number of functional groups available at the surface of the macroporous monolith by post-polymerization modifications. Unfortunately this approach requires at least a two-step fabrication process but this disadvantage is outweighed by the high ion-exchange capacities that can be achieved. Two very different approaches can be employed to impart functionality directly onto the surface of the monolith. One approach is an alternation of the surface chemistry though a chemical reaction that requires the structural monomers to include reactive groups. Typically the monomer GMA is incorporated into the monolithic scaffold, GMA affords epoxide moiety which is vulnerable to ring-opening nucleophilic attack creating a site for covalent attachment for further functional groups. Another approach is to complete a second polymerization reaction on top of the supporting monolithic scaffold; this technique is known as surface grafting.

b) Physical Characterization

Visually, all fabricated monoliths, both the monolith scaffolds utilized for further surface modification and those prepared by co-polymerization, appeared chalky indicating large macropores. The porous properties of all fabricated monoliths were further analyzed by MIP and BET as conformation of this visual assessment. Table 6 contains a summary of the porous properties of all monoliths.

TABLE 6

Summary of the porous properties of monoliths used in this study

| Monolith | Pore diameter (nm) | Specific surface area ($m^2g^{-1}$) |
| --- | --- | --- |
| poly(EDMA-co-MAA) | * | |
| poly(HEMA-co-EDMA-co-SPMA) | 499 | 6.7 |
| poly(GMA-co-DEGMA) | 385 | 8.2 |
| poly(HEMA-co-EDMA) | 600 | |

Figure 3A:
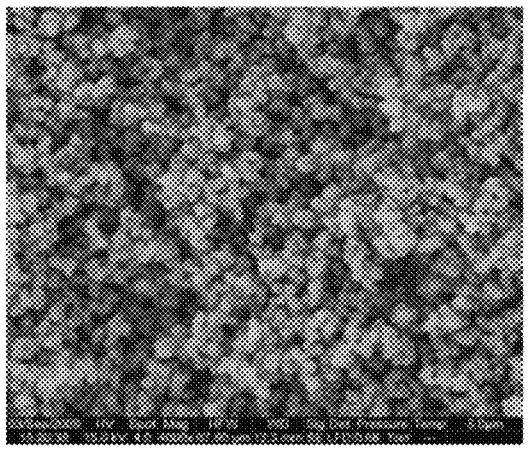
FIGS. 3a-3d show SEM images of the poly(EDMA-co-MAA) (FIG. 3a), poly(HEMA-co-EDMA-co-SPMA) (FIG. 3b), poly(GMA-co-DEDMA) (FIG. 3c) all 4000× magnification, and poly(HEMA-co-EDMA) 6000× magnification (FIG. 3d)
Figure 3B:
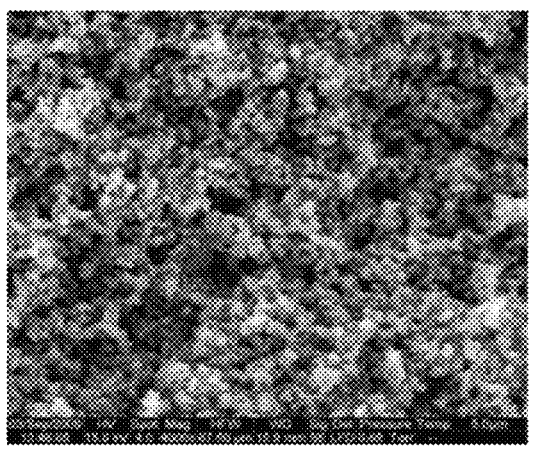
Figure 3C:
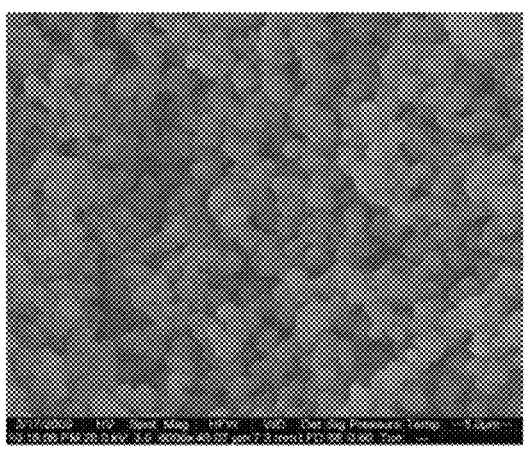
Figure 3D:
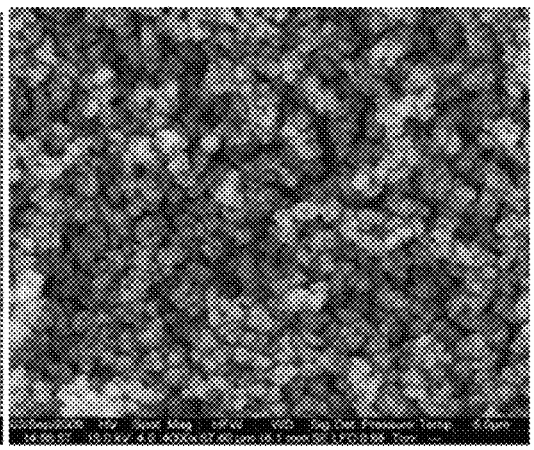

SEM images of both monolithic scaffolds, poly(GMA-co-DEGMA) (FIG. 3a) and poly(HEMA-co-EDMA) (FIG. 3b) were obtained to visualize the morphology of these monoliths. The SEM images also include the co-polymerized materials, poly(EDMA-co-MAA) (FIG. 3c) and poly(HEMA-co-EDMA-co-SPMA) (FIG. 3d). These images clearly indicate a homogenous layer of microglobules and pores of varying diameter.

The ion-exchange capacities of the functionalized sorbents were determined using ion-exchange chromatography and results are pending.

Table 7 demonstrates that sorbents prepared using co-polymerization have a much lower ion-exchange capacity compared with sorbents prepared by postpolymerization surface modification. This result is understood to occur because a certain percentage of the functional monomers are incorporated directly into the polymerization mixture and will therefore be inaccessible at the pore surface and will not contribute to the surface charge.

c) Generic SPE Protocols to Determine the Potential for Selective Extraction and Matrix Elimination Established SPE protocols were employed to investigate the potential of the fabricated ion-exchange sorbents for the selective extraction of target analytes from whole blood and plasma. Initially all sorbents were preconditioned for ionization of the surface groups thus enabling interaction with the target analytes. The SCX and the MSCX sorbents contained sulfonic acid functional groups to enable specific interactions with basic pharmaceutical drugs and the functional groups were ionized in an aqueous solution containing 5% formic acid. The WCX sorbents contained carboxylic acid functional groups; these groups were ionized using an aqueous solution containing 5% ammonium hydroxide.

The SAX sorbent containing quaternary ammonium functional groups was preconditioned using an aqueous solution containing 5% ammonium hydroxide, while the WAX sorbent containing tertiary ammonium functional group was preconditioned using an aqueous solution of 5% formic acid. This enables the selective extraction of acidic pharmaceutical drugs. Preconditioning simply involved soaking the sorbents in an agitated bath of the appropriate aqueous solution for two hours, sorbents were then dried at elevated temperature.

The target analyte employed to investigate potential of the SCX and MSCX sorbents for selective extraction was maraviroc, a moderately basic drug containing an amine group. The potential for selective extraction using WCX sorbents were investigated using UK 258 300 which contains a quaternary amine. The sample was loaded onto the appropriate preconditioned sorbent and affinity was encouraged by implementing an aqueous wash which contained 5% formic acid for the SCX sorbents and 5% ammonium hydroxide for the WCX. A methanol wash was then employed to elute any matrix components that may have adhered to the sorbent due to hydrophobic interactions. Once the matrix components were successfully removed the target analyte could be eluted from the sorbent. SCX protocols utilized a basic eluate buffer, 5% ammonium hydroxide in methanol to elute the target analytes by protonating the sulfonic acid functional group of the sorbent. WCX protocols employ an acidic eluate buffer, 5% formic acid in methanol to elute the target analyte by deprotonating the analyte directly.

Figure 4:
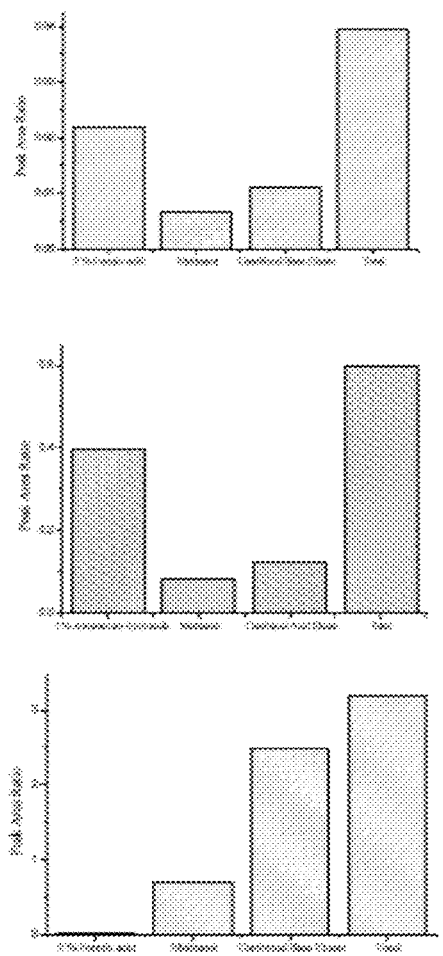
FIG. 4 provides graphs showing the arbitrary MS response of analytes eluted in the binding step, a methanol wash and the eluting buffer, respective MS responses for WCX sorbent (top), MSCX (middle) and SCX (bottom)

The limited ion-exchange capacity of the cation-exchange sorbents prepared by copolymerization is further demonstrated in FIG. 4. The WCX and MSCX sorbents demonstrate a low ion-exchange capacity as the arbitrary MS response indicates that target analyte is eluted during the first wash.

Figure 5:
FIG. 5 shows the depiction of the eluate buffers utilised for the SCX sorbent, aqueous solution of 5% formic acid, methanol, and two 5% ammonium hydroxide eluting buffers in consecutive order.

Much of the unbound or weakly bound matrix components could successfully be removed from the monolithic sorbent by employing the two wash steps. This is demonstrated in FIG. 5 which depicts three consecutive wash steps.

d) Analyses of Functionlised Monolithic Sorbents for Selective Extraction of NCEs i) Analytical Validation of the SCX Sorbent Having fabricated suitable monoliths incorporating cation-exchange functionality for the selective extraction of basic drugs from whole blood and plasma it was necessary to validate the technology in accordance with the Guidance for Industry (Rockville, 2001). The accuracy, precision and sensitivity of recoveries of the pharmaceutical drug maraviroc from the SCX sorbent was investigated using both whole blood and plasma.

Calibration plots of the analyte/internal standard peak ratio (peak area ratio) versus the nominal concentration of maraviroc were constructed with the lower limit of quantification (LLOQ) being 5 ng/mL. A linear response of the MS response over the range of 5 ng/mL-800 ng/ML was observed for both whole blood and plasma, with $r^2=0.995$ and 0.983 respectively.

The inter-assay accuracy and precision of maraviroc using five replicates of each of the four QC standard was determined. The results of the analysis whole blood and plasma analysis are summarized in Table 7 and Table 8.

This exploratory study strongly suggest the selective extraction of is basic NCEs quite possible. The sample was continually transported between 96-well plates which introduced a large degree of error into the obtained results. Furthermore, there was not enough replicates to conclusively determine that the SCX functionalized monolithic sorbent is not suitable for the selective extraction of basic NCEs.

TABLE 7

The inter-assay accuracy and precision for maraviroc in whole rat blood recovered from a SCX sorbent

| Nominal Concentration (ng/mL) | Mean Calculated Concentration (ng/mL) | Standard Deviation | Accuracy (%) | Precision (%) |
|---|---|---|---|---|
| 5 | 3.39 | 1.78 | 148 | 52.42 |
| 20 | 20.28 | 6.33 | 99 | 31.22 |
| 70 | 97.90 | 11.57 | 72 | 11.82 |
| 500 | 661.00 | 187.12 | 76 | 28.31 |

TABLE 8

The inter-assay accuracy and precision for maraviroc in rat plasma recovered from a SCX sorbent

| Nominal Concentration (ng/mL) | Mean Calculated Concentration (ng/mL) | Standard Deviation | Accuracy (%) | Precision (%) |
|---|---|---|---|---|
| 5 | 4.71 | 1.53 | 106 | 32.49 |
| 20 | 12.11 | 4.95 | 165 | 40.85 |
| 70 | 67.85 | 23.74 | 103 | 34.98 |
| 500 | 698.25 | 251.65 | 72 | 36.04 | ii) Analytical Validation of Anion-Exchange Sorbents

The potential for the selective extraction of acidic pharmaceutical drugs using the anion exchange sorbents was investigated in a similar fashion. The target analyte employed to investigate the potential of the SAX sorbent was ibuprofen, while the gabapentin was employed to investigate the potentials of the WAX sorbent. All samples have been prepared for analysis and results are pending. These sorbents were prepared by post-polymerization modifications of a monolithic scaffold and both sorbents afford high ion-exchange capacities. These sorbents may be suitable for the selective extraction of acidic NCEs.

14. Validation of Poly(HEMA-co-EDMA) for Dried Blood Spot Sampling a. Preparation of Standards.

Primary stocks of the analyte fluconazole were prepared in dimethyl sulfoxide (DMSO) at 1 mg/mL. Working standards of were prepared from the primary stock at 1000, 100 and 1 µg/mL in water:methanol (9:1v/v). The internal standard (IS), deuterated fluconazole ($d_8$), was also prepared at 1 µg/mL in DMSO. Working solutions of the internal standard (IS) were prepared at 10000 and 1000 ng/mL in the aqueous solution. The primary solution was stored at 4° C. and brought to room temperature before use. All working standards were prepared on the same day as analysis.

Calibration standards were prepared by a dilution of the appropriate working solution in biological matrices (whole blood and plasma). Calibrant concentrations were 10, 30, 50, 100, 200, 400, 800, 1000 and 2000 ng/mL and each calibrant contained 100 ng/mL of IS. The calibration curve also included a blank monolith sample disk (double blank), a blank matrix sample disk (blank) and matrix disk containing only IS (zero blank). Quality control (QC) standards are prepared from separate primary stock solutions to those used for the calibration standard. QC samples were prepared in the appropriate matrix at concentrations of 20, 70, 500 and 800 ng/mL. A water:methanol solution (9:1 v/v) was spiked with 60 ng/mL of analyte and 7.5 ng/mL of the IS (termed solution A). Homogeneity of all samples was ensured by vigorous mixing.

b. Sample Processing.

Aliquots (15 µL) of each standard were spotted directly onto the sorbent. Spots were left to adsorb at room temperature for approximately 1 h, after which a hole punch (Harris Unicore, Ted Pella) was used to remove the entire blood spot from the bulk material. Sample disks were placed in a 2 mL square 96-well filter plate (Strata Impact Protein Precipitation Plate, Phenomenex) for a further 1 h to ensure that they were completely dried. The analyte was extracted using 300 µL of methanol on a flat bed mixer (Heidolph Instruments) at 1300 rpm for 30 min. Samples were filtered into a 2 mL 96-well polypropylene plate using a vacuum manifold system (TomtecInc). The filtrate was evaporated under a stream of $N_2$ at 55° C. and samples were reconstituted with 200 µL of water:methanol (9:1 v/v).

c. HPLC-MS/MS Analysis.

The analytical system consisted of a CTC HTS PAL autosampler (Presearch), an Agilent 1100 series binary pump (Agilent) and a 4000 QTRAP mass spectrometer (Applied Bioscience, Sciex). The system was operated using the software Analyst 1.4.2.

Chromatographic separations were achieved using a standard reversed phase monolithic column, Onyx $C_{18}$ (3.00× 100 mm) (Phenomenex). A simple solvent gradient (aqueous, organic, aqueous) was employed to elute the analyte, the mobile phases employed were mobile phase A (water: methanol 9:1 v/v) and mobile phase B (water:methanol 1:9 v/v). Following sample injection (40 µL) the mobile phase was held constant from 0 to 0.10 mins at 90% A and 10% B. A ballistics gradient was employed between 0.10 and 1.10 min ceasing when composition of mobile phase was 5% A and 95% A. After which it was returned to 90% A and 10% B from 1.10 to 3.10 min. The mobile phase then remained constant from 3.10 to 3.50 min. The mobile phase was pumped through the system at flow rate of 1.00 mL/min and the column was maintained at room temperature.

The mass spectrometer detector was equipped with a TurboSpaylon source with a source temperature set at a temperature of 700° C. The detector was operated in positive ion multiple reaction monitoring (MRM) mode. The scanning MRM transitions were 307.00 to 238.00 m/z and 315.00 to 244.00 m/z for analyte and IS respectively. The optimised dwell time was 76 msec and 71 msec respectively and the collision energy was optimized at 23 eV for both analytes.

d. Bioanalytical Validation.

Selectivity (Interfering Compounds), Recovery, Matrix Effects and Sensitivity.

Double blank and blank samples from six individual sources were prepared as above. These samples were analysed to gauge the presence of interfering compounds that may have a similar retention time as the analyte. The potential of interferences in monolith and both matrices was assessed. The recovery could be determined by comparing the peak area of an extracted high QC sample to an unextracted sample (blank sample disks reconstituted in solution A). Matrix effects were considered by a comparison of the analyte/IS peak area of a direct injection of solution A to the peak area of an unextracted sample. At least two individual matrix sources were employed The sensitivity, or determination of the lower limit of quantification (LLOQ) was determined through a comparison of the double blank and black samples to low concentrations of non-zero samples.

Calibration Curve, Reproducibility and Carry Over.

The double blank, blank and zero-blank along with nine non-zero calibration standards were prepared in duplicate to determine reproducibility. A $1/x^2$ regression model was applied to the data. Instrumental carry over was determined by injecting a blank sample directly after the highest calibration standard while sample preparation carry over was assessed by including a blank sample disk that had been punched from the bulk monolith following the highest calibrant standard.

Accuracy and Precision.

The intra-assay accuracy and precision was determined by assaying six replicates at each of the four QC concentrations. The inter-assay accuracy and precision was determined by assaying each of the six samples at each QC level 3 times.

Dilution Above the Higher Limits of Quantification (HLQ).

Biological matrices were spiked with 20000 ng/mL (10× the HLQ). Six replicates were spotted onto the sorbent. Samples were processed as outlined above. Diluent samples were prepared by extracting 36 sample blank sample disks with 7.2 mL of 9:1 v/v H2O:methanol. A 10 µL aliquot of each of the concentrated samples was then diluted in 390 µL of the diluent.

e. Results and Discussion of Bioanalytical Method Validation

Selectivity and Sensitivity

Figures 6A, 6B, 6C:
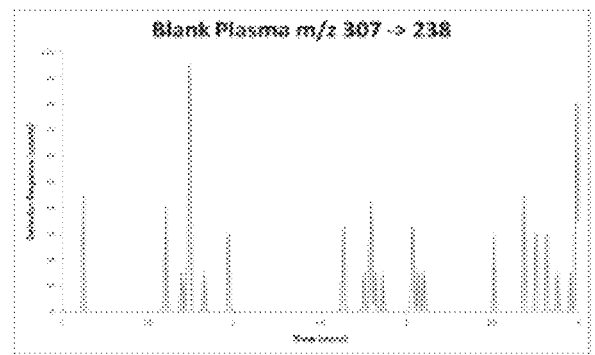
FIGS. 6a-6c provide graphs showing LC-MS/MS chromatograms of double blank and blank matrix samples.
Figure 7A:
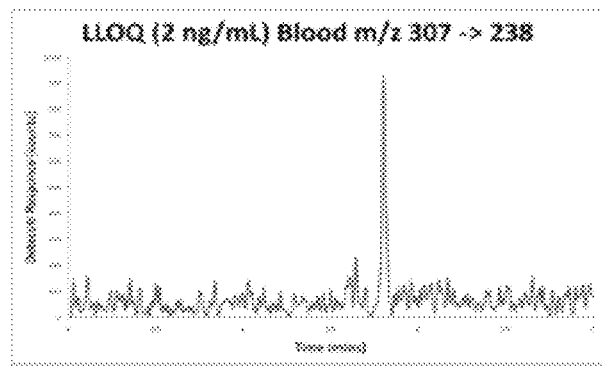
FIGS. 7a-7c provide graphs showing LC-MS/MS chromatograms of the LLOQ, highest calibrant and IS peaks in blood (top to bottom).
Figure 7B:
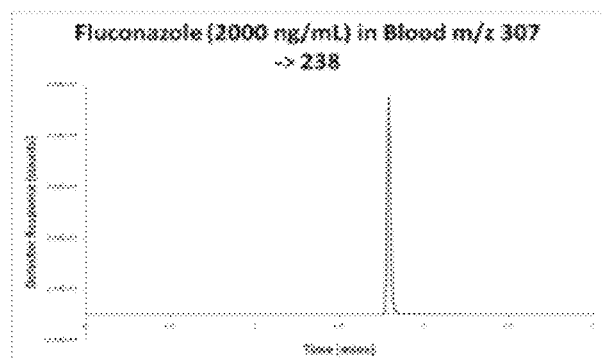
Figure 7C:
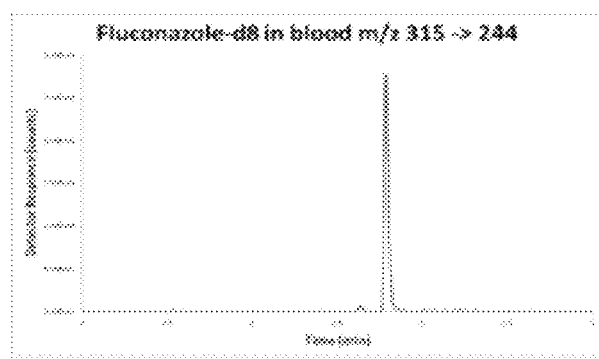

Both the poly(HEMA-co-EDMA) sorbent and the biological matrices have the potential to contain co-eluting components that may enhance or suppress ionization consequently interfering with the quantification of fluconazole. The chromatographic profiles were assessed using the selected MRM transition m/z 307-238 (analyte) and m/z 315-244 (IS). FIGS. 6a-6c display LC-MS/MS profiles of the double blank and blanks samples of both blood and plasma. Fluconazole and its deuterated IS had a typical retention time of 1.8 minutes (FIGS. 7a-7c) and from these profiles it can be seen that there are no significant interferences in this region. At least six different sources of the double blank and blanks samples (n=9) were assessed to determine if samples theses results were consistent. The average detector response at 1.8 min was 82, 254 and 101 counts for double blank, plasma blank and blood blanks respectively (FIGS. 6a-6c). The standard operating procedure (SOPs) for bioanalytical method validation for chromatographic methods of analyte concentration determination state that any response with a similar retention time to the analyte must be ≤20% of the response of the lower limit of quantification (LLOQ) calibrations standard. For the current validation the LLOQ was to be 2 ng/mL and 5 ng/mL respectively for blood and plasma. At these concentrations the overall average detector response was 1176 counts in blood and 8814 counts in plasma (n=18). These results elute to the possibility of further reducing the level of quantification. The average detector response for the deuterated IS in the zero blank was $4.255 \times 10^4$ counts and $4.205 \times 10^4$ counts (n=2) for blood and plasma. The SOP states that any response with a similar retention time to the IS must be ≤5% of the IS.

Matrix Effects and Recovery.

The extraction recovery could be calculated by formula 1. while formula 2. was employed to determine the overall recovery.

Extraction Recovery=Extracted QC sample/Unextracted Sample×100 (1)

Overall Recovery=Extracted QC sample/Solution $A$×100 (2)

The average extraction recovery for fluconazole and fluconazole-$d_8$ from a dried blood spot (DBS) sample was 85 and 77% respectively with the average overall recovery at 76 and 71%. These results indicate that there is no major loss of the analytes in the extraction process. The results of the DPS extraction recovery for analyte and IS are 108 and 52% respectively while overall 79 and 32% of the drug were recovered, which were found to be less reliable than for DBS results.

The matrix effects arising from the monolith and biological matrices were calculated using formula 3.

Matrix Effects=(Unextracted sample disk/solution $A$−1)×100 (3)

Results of this analysis can be seen in Table 9, these results suggest matrix suppression is occurring. No samples of the 20 trialled indicated that any signal enhancement was occurring. While the monolith and the blood sample show no significant signs of matrix suppression the plasma results were much higher than expected.

TABLE 9

Matrix effects (n = 20)

| Sample | Fluconazole | Fluconazole-$d_8$ |
|---|---|---|
| Monolith | −5 | −3 |
| Plasma | −28 | −26 |
| Blood | −10 | −6 |

DBS and DPS Assay Performance Characteristics.

Calibration plots of the analyte/IS peak area ratio versus then nominal concentration of the calibrant standards in both blood and plasma were constructed. A linear response for both the DBS and DPS samples was observed over the concentration range and this linear response was reproducible for all calibration curves assessed (blood=4 and plasma=2). Carry over of the analytical processed was evaluated with both the carry over from the sample preparation procedures and the carry over analysis being analysed. In both instances the carry over fell well short of 1% for both plasma and blood and was thus determined to be negligible. The intra- and inter-assay accuracy and precision for DBS is summarised in Table 10. All values obtained were in compliance with the internationally recognised acceptance criteria for assay validations (i.e. accuracy and precision should fall within 15% of the nominal at each QC level, while at the LLOQ the accuracy and precision may vary by 20%).

TABLE 10

The intra- and inter- assay performance data for fluconazole in DBS samples (n = 6) at each concentration level.

| | | Nominal Concentration (ng/mL) | | | |
|---|---|---|---|---|---|
| | | 20 | 70 | 500 | 800 |
| Batch 1 | Average concentration (ng/mL) | 17.35 | 66.33 | 488.67 | 724.00 |

TABLE 10-continued

The intra- and inter- assay performance data for fluconazole in DBS samples (n = 6) at each concentration level.

| | | Nominal Concentration (ng/mL) | | | |
|---|---|---|---|---|---|
| | | 20 | 70 | 500 | 800 |
| | SD | 0.965 | 3.637 | 13.938 | 23.512 |
| | Accuracy | 13 | 5 | 2 | 10 |
| | Precision | 6 | 5 | 3 | 3 |
| Batch 2 | Average concentration (ng/mL) | 20.32 | 66.33 | 530.00 | 878.80 |
| | SD | 0.941 | 3.637 | 7.849 | 45.730 |
| | Accuracy | 2 | 5 | 6 | 10 |
| | Precision | 5 | 5 | 1 | 5 |
| Batch 3 | Average concentration (ng/mL) | 18.25 | 71.12 | 465.60 | 787.83 |
| | SD | 0.989 | 1.376 | 44.405 | 22.275 |
| | Accuracy | 9 | 2 | 7 | 2 |
| | Precision | 5 | 2 | 10 | 3 |
| Overall inter-assay | Average concentration (ng/mL) | 18.25 | 71.12 | 465.60 | 803.21 |
| | SD | 1.11 | 2.50 | 85.00 | 29.43 |
| | Accuracy | 7 | 3 | 6 | 0 |
| | Precision | 6 | 4 | 5 | 4 |

Table 11 summarises the intra- and inter-assay accuracy and precision for DPS samples. Only one batch of assays was completed, although further supporting trials are underway.

The average concentration of blood samples (n=3) being 1483 ng/mL while the average concentration of plasma samples (n=6) was 1360. The accuracy and precision for the assay was 26 and 16% respectively for blood and 32 and 7% for plasma.

TABLE 11

The intra- and inter- assay performance data for fluconazole in DPS samples (n = 6) at each concentration level.

| | | Nominal Concentration (ng/mL) | | | |
|---|---|---|---|---|---|
| | | 20 | 70 | 500 | 800 |
| Batch 1 | Average concentration (ng/mL) | 20.12 | 69.35 | 496.17 | 805.83 |
| | SD | 0.627 | 3.173 | 23.319 | 23.164 |
| | Accuracy | 1 | 1 | 1 | 1 |
| | Precision | 3 | 5 | 5 | 3 |
| Overall inter-assay | Average concentration (ng/mL) | 20.11 | 68.2 | 495.50 | 810.833 |
| | SD | 0.60 | 3.18 | 17.95 | 15.502 |
| | Accuracy | 1 | 3 | 1 | 1 |
| | Precision | 3 | 5 | 4 | 2 |

Preliminary data on the stability of fluconazole and fluconazole-$d_8$ was also obtained. The stability of compounds in the primary stock solution and working solutions are being investigated for the intended period of use. This can be assessed simply assessing the peak area of the analyte between samples ($t_0$ and $t_\infty$). The stability of the analyte/IS in the biological matrices (liquid) is also being assessed along with the stability analyte/IS in the DBS and DPS samples stored short term and long term (typically stored in a desiccator). These parameters can be assessed analysing against a freshly prepared calibration curve and comparing to fresh samples. Any degradation of the compound is determined by a reduction in the concentration of the QC sample.

The invention claimed is:

1. A method of storing whole blood for analysis comprising:
   applying a whole blood sample directly to a formed porous polymer monolith medium, said porous polymer monolith comprising an integral body with a pore size and/or specific surface area adapted to facilitate the drying and storage of body fluids; wherein the pore size of the porous polymer monolith is in the range of 50 to 5,000 nm and the specific surface area of the porous polymer matrix when measured by nitrogen adsorption using BET isotherm is in the range of 0.5 to 1000 $m^2/g$;
   drying the whole blood sample such that the whole blood sample at least partially solidifies and adsorbs or adheres to the formed porous polymer monolith medium; and
   storing the sample adsorbed or adhered to the formed porous polymer monolith medium.

2. A method of storing whole blood for analysis comprising:
   applying one or more whole blood samples directly to one or more regions of a formed porous polymer monolith medium, said porous polymer monolith comprising an integral body with a pore size and/or specific surface area adapted to facilitate the drying and storage of body fluids; wherein the pore size of the porous polymer monolith is in the range of 50 to 5,000 nm and the specific surface area of the porous polymer matrix when measured by nitrogen adsorption using BET isotherm is in the range of 0.5 to 1000 $m^2/g$;
   partially drying the one or more whole blood samples applied to the formed porous polymer monolith medium;
   separating any one or more regions of the formed porous polymer monolith medium having the one or more whole blood samples applied thereto, from one or more regions of the formed porous polymer monolith medium without sample applied thereto;
   further drying the one or more whole blood samples applied to the one or more regions of the formed porous polymer monolith medium; and
   storing the one or more whole blood samples applied to the one or more regions of the formed porous polymer monolith medium.

3. The method according to claim 1, wherein the drying of the whole blood sample is enhanced by application of at least one of elevated temperature and forced convection.

4. The method according to claim 3, wherein the elevated temperature is 90° C. or above.

5. The method according to claim 1, further comprising identifying and detecting an analyte from the stored whole blood sample adsorbed or adhered to the formed porous polymer monolith medium.

6. The method according to claim 5, wherein the stored whole blood sample is analysed without pre-treatment or removal of the whole blood sample adsorbed or adhered to the formed porous polymer monolith medium.

7. The method according to claim 1, wherein the formed porous polymer monolith medium is formed from one or more acrylic acid monomers optionally functionalised with a group selected from sulphonyl, phosphonyl, carboxyl, amino and nitro.

8. The method according to claim 7, wherein the acrylic acid monomers are optionally functionalised methacrylates selected from at least one of hydroxyethylmethacrylate, methacrylic acid, ethylene glycol dimethacrylic acid, or combinations thereof.

9. The method according to claim 8, wherein the formed porous polymer monolith medium is obtained from a polymerization mixture comprising 10 to 40 vol % of a monovinyl monomer, 10 to 40 vol % of a polyvinyl monomer, 20 to 80 vol % porogens, and 1 vol % initiator.

10. The method according to claim 1, wherein the formed porous polymer monolith medium comprises a copolymer of a polyvinyl monomer and a monovinyl monomer.

* * * * *